(12) United States Patent
Ksander et al.

(10) Patent No.: US 7,652,061 B2
(45) Date of Patent: Jan. 26, 2010

(54) N-ACYL NITROGEN HETEROCYCLES AS LIGANDS OF PEROXISOME PROLIFERATOR-ACTIVATED RECEPTORS

(75) Inventors: Gary Michael Ksander, Amherst, NH (US); Thalaththani Ralalage Vedananda, Shrewsbury, MA (US)

(73) Assignee: Novartis A.G., Basel (CH)

( * ) Notice: Subject to any disclaimer, the term of this patent is extended or adjusted under 35 U.S.C. 154(b) by 327 days.

(21) Appl. No.: 10/556,988

(22) PCT Filed: May 19, 2004

(86) PCT No.: PCT/EP2004/005434

§ 371 (c)(1), (2), (4) Date: Feb. 3, 2006

(87) PCT Pub. No.: WO2004/103995

PCT Pub. Date: Dec. 2, 2004

(65) Prior Publication Data

US 2006/0135593 A1    Jun. 22, 2006

Related U.S. Application Data

(60) Provisional application No. 60/472,067, filed on May 20, 2003.

(51) Int. Cl.
*A61K 31/40* (2006.01)
*C07D 207/08* (2006.01)

(52) U.S. Cl. .................. 514/423; 548/235; 548/533; 514/374

(58) Field of Classification Search .......... 548/235, 548/533; 514/374, 423
See application file for complete search history.

(56) References Cited

U.S. PATENT DOCUMENTS 5,045,540 A * 9/1991 Hodges et al. ............ 514/235.8

FOREIGN PATENT DOCUMENTS

EP    0 915 088    5/1999
WO    WO 00/59874    10/2000
WO    WO 03/043985    5/2003

OTHER PUBLICATIONS

Ernsberger, et al. "Metabolic actions of angiotensin receptor antagonists: PPAR-γ agonist actions or a class efect?", Current Opinion in Pharmacology, vol. 7, pp. 140-145 (2007).*
Collins et al., *N*-(2-Benzoylphenyl)-L-tyrosine PPARγ Agonists. 2. Structure—Activity Relationship and Optimization of the Phenyl Alkyl Ether Moiety, *J Med Chem*, vol. 41, No. 25, pp. 5037-5054 (1998).
Gante, Kahlenberg, Lauterbach and Weitzel, "Peptidsynethese, I. Über eine neue Carbonsäureamid-Synthese", *Chemiker-Zeitung*, vol. 109, pp. 155-156 (1985).
Rami and Smith, "Synthetic Ligans for PPARγ—Review of Patent Literature 1994-1999", *Exp Opin Ther Patents*, vol. 10, No. 5, pp. 623-634 (2000).
Willson and Wahli, "Peroxisome Proliferator-activated Receptor Agonists", *Curr Opin Chem Biol*, vol. 10, pp. 235-241 (1997).

* cited by examiner

*Primary Examiner*—Joseph K. McKane
*Assistant Examiner*—Janet L Coppins
(74) *Attorney, Agent, or Firm*—Theresa A. Devlin

(57) ABSTRACT

Compounds of the formula

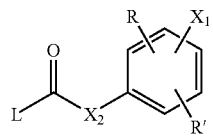

(I)

provide pharmacological agents which bind to Peroxisome Proliferator-Activated Receptors (PPARs). Accordingly, the compounds of the instant invention are useful for the treatment of conditions mediated by the PPAR receptor activity in mammals. Such conditions include dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, inflammatory bowel diseases, ulcerative colitis, Crohn's disease, and conditions in which impaired glucose tolerance, hyperglycemia and insulin resistance are implicated, such as type-1 and type-2 diabetes, and Syndrome X.

14 Claims, No Drawings

N-ACYL NITROGEN HETEROCYCLES AS LIGANDS OF PEROXISOME PROLIFERATOR-ACTIVATED RECEPTORS

This application claims benefit of U.S. Provisional Application 60/472,067, filed May 20, 2003.

The present invention relates to heterocyclic compounds, to pharmaceutical compositions containing them, and to methods of treating conditions mediated by the Peroxisome Proliferator-Activated Receptor (PPAR) activity by employing such compounds.

Accordingly, the present invention provides compounds of the formula

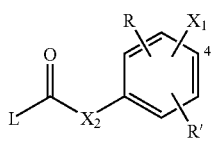

(I)

wherein L is a radical selected from the group consisting of:

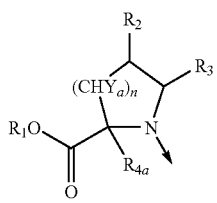

(II)

and

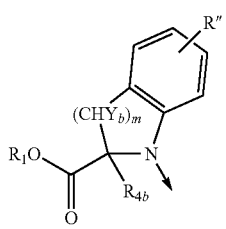

(III)

in which $R_1$ is hydrogen, optionally substituted alkyl, aryl, heteroaryl, aralkyl or cycloalkyl;

$R_2$ is hydrogen, hydroxy, oxo, optionally substituted alkyl, aryl, aralkyl, alkoxy, aryloxy, aralkoxy, alkylthio, arylthio or aralkylthio;

$R_3$ is hydrogen; or $R_2$ and $R_3$ combined are alkylene which together with the carbon atoms to which they are attached form a fused 5 to 7-membered ring; or $R_2$ and $R_3$ combined are a bond between the carbon atoms to which they are attached;

n is zero or an integer of 1 or 2;

$Y_a$ is hydrogen; or $Y_a$ and $R_2$ combined are a bond between the carbon atoms to which they are attached;

$R_{4a}$ is hydrogen; or $R_{4a}$ and $Y_a$ combined are a bond between the carbon atoms to which they are attached;

R" is hydrogen, optionally substituted alkyl, alkoxy or halogen;

m is an integer of 1 or 2;

$Y_b$ is hydrogen;

$R_{4b}$ is hydrogen; or $R_{4b}$ and $Y_b$ combined are a bond between the carbon atoms to which they are attached;

R and R' are independently hydrogen, halogen, optionally substituted alkyl, alkoxy, aralkyl or heteroaralkyl; or R and R' combined together with the carbon atoms to which they are attached form an optionally substituted fused 5- to 6-membered aromatic or heteroaromatic ring provided that R and R' are attached to carbon atoms adjacent to each other; or R—C and R'—C may independently be replaced by nitrogen;

$X_1$ is -Z-$(CH_2)_p$-Q-W wherein

Z is a bond, O, S, S(O) or $S(O)_2$; or

Z is —C(O)$NR_5$— in which $R_5$ is hydrogen, alkyl or aralkyl;

p is an integer from 1 to 8;

Q is a bond; or

Q is —O$(CH_2)_r$— or —S$(CH_2)_r$— in which r is zero or an integer from 1 to 8; or Q is —O$(CH_2)_{1-8}$O—, —S$(CH_2)_{1-8}$O—, —S$(CH_2)_{1-8}$S— or —C(O)—; or Q is —C(O)$NR_6$— in which $R_6$ is hydrogen, optionally substituted alkyl, cycloalkyl, aryl, heteroaryl, aralkyl or heteroaralkyl; or Q is —$NR_7$—, —$NR_7$C(O)—, —$NR_7$C(O)$NR_8$— or —$NR_7$C(O)O— in which $R_7$ is hydrogen, optionally substituted alkyl, cycloalkyl, aryl, heteroaryl, aralkyl or heteroaralkyl;

$R_8$ is hydrogen, alkyl or aralkyl;

W is cycloalkyl, aryl, heterocyclyl, aralkyl or heteroaralkyl; or

W and $R_6$ taken together with the nitrogen atom to which they are attached form a 8- to 12-membered bicyclic ring, which may be optionally substituted or may contain another heteroatom selected from oxygen, nitrogen and sulfur;

$X_2$ is —$C(R_9)_2$, O, S or —$NR_{10}$— in which $R_9$ is hydrogen or lower alkyl;

$R_{10}$ is hydrogen, alkyl or aralkyl;

provided that W is not 2-methylquinolin-4-yl when Z is O, p is 1, Q is a bond, $X_2$ is —$C(R_9)_2$— in which $R_9$ is hydrogen, and $X_1$ is located at the 4-position; or W is not 2-butyl-4-chloro-5-hydroxymethylimidazol-1-yl when Z is a bond, p is 1, Q is a bond, $X_2$ is —$NR_{10}$— in which $R_{10}$ is hydrogen, and $X_1$ is located at the 4-position;

or an optical isomer thereof; or a mixture of optical isomers thereof; or a pharmaceutically acceptable salt thereof.

The compounds of the present invention bind to the Peroxisome Proliferator-Activated Receptors (PPARs) and, thus, the present invention provides pharmaceutical agents for the treatment of conditions mediated by the PPAR activity in mammals. Such conditions include dyslipidemia, hyperlipidemia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, inflammatory bowel diseases (IBDs), ulcerative colitis, Crohn's disease, and conditions in which impaired glucose tolerance, hyperglycemia and insulin resistance are implicated such as type-1 and type-2 diabetes, and Syndrome X.

Listed below are definitions of various terms used to describe the compounds of the instant invention. These definitions apply to the terms as they are used throughout the specification unless they are otherwise limited in specific instances either individually or as part of a larger group, e.g., wherein an attachment point of a certain group is limited to a specific atom within that group, the point of attachment is defined by an arrow at the specific atom.

The term "optionally substituted alkyl" refers to unsubstituted or substituted straight or branched chain hydrocarbon groups having 1 to 20 carbon atoms, preferably 1 to 7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, cycloalkyl, alkanoyl, alkoxy, alkyloxyalkoxy, alkanoyloxy, amino, alkylamino, dialkylamino, alkanoylamino, thiol, alkylthio, alkylthiono, alkylsulfonyl, arylsulfonyl, heteroarylsulfonyl, sulfonamido, nitro, cyano, carboxy, alkoxycarbonyl, aryl, alkenyl, alkynyl, aralkoxy, guanidino, heterocyclyl including indolyl, imidazolyl, furyl, thienyl, thiazolyl, pyrrolidyl, pyridyl, pyrimidyl, piperidyl, morpholinyl and the like.

The term "lower alkyl" refers to those alkyl groups as described above having 1 to 7, preferably 1 to 4 carbon atoms.

The term "halogen" or "halo" refers to fluorine, chlorine, bromine and iodine. The term "alkenyl" refers to any of the above alkyl groups having at least two carbon atoms and further containing a carbon to carbon double bond at the point of attachment. Groups having two to four carbon atoms are preferred.

The term "alkynyl" refers to any of the above alkyl groups having at least two carbon atoms and further containing a carbon to carbon triple bond at the point of attachment. Groups having two to four carbon atoms are preferred.

The term "alkylene" refers to a straight chain bridge of 1 to 6 carbon atoms connected by single bonds (e.g., —(CH$_2$)$_x$— wherein x is 1 to 6), which may be interrupted with one or more heteroatoms selected from oxygen, sulfur and nitrogen, and may be substituted with 1 to 3 substituents such as alkyl, alkoxy, halo, hydroxy, cycloalkyl, alkanoyl, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, aralkoxy, guanidino, heterocyclyl including indolyl, imidazolyl, furyl, thienyl, thiazolyl, pyrrolidyl, pyridyl, pyrimidyl, piperidyl, morpholinyl and the like The term "cycloalkyl" refers to optionally substituted monocyclic, bicyclic or tricyclic hydrocarbon groups of 3 to 12 carbon atoms, each of which may optionally be substituted by one or more substituents, such as alkyl, halo, oxo, hydroxy, alkoxy, alkanoyl, amino, alkylamino, dialkylamino, thiol, alkylthio, nitro, cyano, carboxy, carboxyalkyl, alkoxycarbonyl, alkyl- and arylsulfonyl, sulfonamido, heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.

The term "acyl" refers to alkanoyl, aroyl, heteroaroyl, arylalkanoyl or heteroarylalkanoyl.

The term "alkanoyl" refers to alkyl-C(O)—.

The term "alkanoyloxy" refers to alkyl-C(O)—O—.

The terms "alkylamino" and "dialkylamino" refer to alkyl-NH— and (alkyl)$_2$N—, respectively.

The term "alkanoylamino" refers to alkyl-C(O)—NH—.

The term "alkylthio" refers to alkyl-S—.

The term "alkylaminothiocarbonyl" refers to alkyl-NHC(S)—.

The term "trialkylsilyl" refers to (alkyl)$_3$Si—.

The term "trialkylsilyloxy" refers to (alkyl)$_3$SiO—.

The term "alkylthiono" refers to alkyl-S(O)—.

The term "alkylsulfonyl" refers to alkyl-S(O)$_2$—.

The term "alkoxycarbonyl" refers to alkyl-O—C(O)—.

The term "alkoxycarbonyloxy" refers to alkyl-O—C(O)O—.

The term "carbamoyl" refers to alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)— and alkyl(aralkyl)-NC(O)—.

The term "aryl" refers to monocyclic or bicyclic aromatic hydrocarbon groups having 6 to 12 carbon atoms in the ring portion, such as phenyl, naphthyl, tetrahydronaphthyl, biphenyl and diphenyl groups, each of which may optionally be substituted by one to four substituents, such as alkyl, halo, hydroxy, alkoxy, alkanoyl, alkanoyloxy, optionally substituted amino, thiol, alkylthio, nitro, cyano, carboxy, carboxyalkyl, alkoxycarbonyl, alkylthiono, alkyl- and arylsulfonyl, sulfonamido, heterocycloyl and the like.

The term "monocyclic aryl" refers to optionally substituted phenyl as described under aryl.

The term "aralkyl" refers to an aryl group bonded directly through an alkyl group, such as benzyl.

The term "aralkylthio" refers to aralkyl-S—.

The term "aralkoxy" refers to an aryl group bonded directly through an alkoxy group.

The term "arylsulfonyl" refers to aryl-S(O)$_2$—.

The term "arylthio" refers to aryl-S—.

The term "aroyl" refers to aryl-C(O)—.

The term "aroylamino" refers to aryl-C(O)13 NH—.

The term "aryloxycarbonyl" refers to aryl-O—C(O)—.

The term "heterocyclyl" or "heterocyclo" refers to an optionally substituted, fully saturated or unsaturated, aromatic or non-aromatic cyclic group, for example, which is a 4- to 7-membered monocyclic, 7- to 12-membered bicyclic, or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, triazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents selected from the group consisting of:
(a) alkyl;
(b) hydroxy (or protected hydroxy);
(c) halo;
(d) oxo (i.e. =O);
(e) optionally substituted amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfonamido, sulfonamidoalkyl, sulfonamidoaryl or sulfonamidodialkyl;
(o) alkylcarbonyloxy;
(p) arylcarbonyloxy;
(q) arylthio;
(r) aryloxy;
(s) alkylthio;
(t) formyl;
(u) carbamoyl;
(v) aralkyl; or
(w) aryl substituted with alkyl, cycloalkyl, alkoxy, hydroxy, amino, alkylamino, dialkylamino or halo.

The term "heterocyclooxy" denotes a heterocyclic group bonded through an oxygen bridge.

The term "heteroaryl" refers to an aromatic heterocycle, for example monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like; optionally substituted by, e.g., lower alkyl, lower alkoxy or halo.

The term "heteroarylsulfonyl" refers to heteroaryl-$S(O)_2$—.

The term "heteroaroyl" refers to heteroaroyl-C(O)—.

The term "heteroaralkyl" refer to a heteroaryl group bonded through an alkyl group.

Pharmaceutically acceptable salts of any compound of the present invention refer to salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris(hydroxymethyl)-methyl-ammonium salts, and salts with amino acids.

Similarly acid addition salts, such as those formed with mineral acids, organic carboxylic acids and organic sulfonic acids, e.g., hydrochloric acid, maleic acid and methanesulfonic acid, are possible provided a basic group, such as pyridyl or oxazolyl, constitutes part of the structure.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono or disubstituted lower alkyl esters such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester, and the like conventionally used in the art.

The compounds of the invention depending on the nature of the substituents, may possess one or more asymmetric centers. The resulting diastereoisomers, optical isomers, i.e., enantiomers, and geometric isomers are encompassed by the instant invention.

As described herein above, the present invention provides phenylacetic acid derivatives of formula (1), pharmaceutical compositions containing them, methods for preparing such compounds and methods of treating conditions mediated by the PPAR activity by administration of a therapeutically effective amount of a compound of the present invention or a pharmaceutical composition thereof.

Preferred are the compounds of formula (I) having the formula

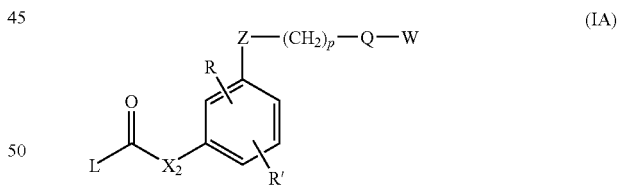

(IA)

wherein L is a radical selected from the group consisting of:

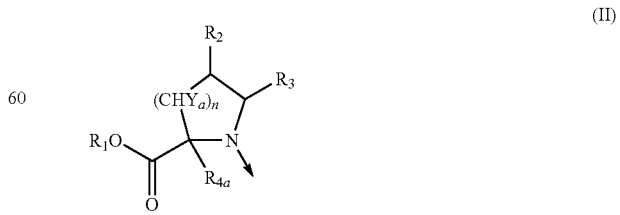

(II)

and

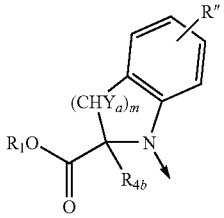

(III)

in which
R₁ is hydrogen, optionally substituted alkyl, aryl, heteroaryl, aralkyl or cycloalkyl;
R₂ is hydrogen, hydroxy, oxo, optionally substituted alkyl, aryl, aralkyl, alkoxy, aryloxy, aralkoxy, alkylthio, arylthio or aralkylthio;
R₃ is hydrogen; or
R₂ and R₃ combined are alkylene which together with the carbon atoms to which they are attached form a fused 5- to 7-membered ring; or
R₂ and R₃ combined are a bond between the carbon atoms to which they are attached;
n is 1;
Y$_a$ is hydrogen; or
Y$_a$ and R₂ combined are a bond between the carbon atoms to which they are attached;
R$_{4a}$ is hydrogen; or
R$_{4a}$ and Y$_a$ combined are a bond between the carbon atoms to which they are attached;
R" is hydrogen, optionally substituted alkyl, alkoxy or halogen;
m is 1;
Y$_b$ is hydrogen;
R$_{4b}$ is hydrogen; or
R$_{4b}$ and Y$_b$ combined are a bond between the carbon atoms to which they are attached;
R and R' are independently hydrogen, halogen, optionally substituted alkyl, alkoxy, aralkyl or heteroaralkyl; or
R and R' combined together with the carbon atoms to which they are attached form an optionally substituted fused 5- to 6-membered aromatic or heteroaromatic ring provided that R and R' are attached to carbon atoms adjacent to each other; or
Z is a bond, O or S;
p is an integer from 1 to 8;
Q is a bond; or
Q is —O(CH₂)$_r$— or —S(CH₂)$_r$— in which
r is zero or an integer from 1 to 8; or
Q is —C(O)NR₆— in which
R₆ is hydrogen, optionally substituted alkyl, cycloalkyl, aryl, heteroaryl, aralkyl or heteroaralkyl; or
Q is —NR₇—, —NR₇C(O)—, —NR₇C(O)NR₈— or —NR₇C(O)O— in which
R₇ is hydrogen, optionally substituted alkyl, cycloalkyl, aryl, heteroaryl, aralkyl or heteroaralkyl;
R₈ is hydrogen, alkyl or aralkyl;
W is cycloalkyl, aryl, heterocyclyl, aralkyl or heteroaralkyl; or
W and R₆ taken together with the nitrogen atom to which they are attached form a 8- to 12-membered bicyclic ring, which may be optionally substituted or may contain another heteroatom selected from oxygen, nitrogen and sulfur;
X₂ is —C(R₉)₂—, O, S or —NR₁₀— in which R₉ is hydrogen or lower alkyl;
R₁₀ is hydrogen or lower alkyl;
or an optical isomer thereof; or a mixture of optical isomers thereof; or a pharmaceutically acceptable salt thereof.

Preferred are the compounds of formula (IA) wherein
R₁ is hydrogen or optionally substituted alkyl;
R₂ and R₃ are hydrogen;
Y$_a$ and Y$_b$ are hydrogen;
R$_{4a}$ and R$_{4b}$ are hydrogen;
R and R' are independently hydrogen, halogen, optionally substituted C$_{1-6}$alkyl or C$_{1-6}$ alkoxy;
p is an integer from 1 to 5;
Q is a bond; or
Q is —O(CH₂)$_r$— or —S(CH₂)$_r$— in which
r is zero or 1; or
Q is —C(O)NR₆— in which
R₆ is hydrogen or lower alkyl; or
Q is —NR₇—, —NR₇C(O)—, —NR₇C(O)NR₈— or —NR₇C(O)O— in which
R₇ is hydrogen or optionally substituted alkyl;
R₈ is hydrogen or alkyl;
X₂ is —C(R₉)₂—, O, S or —NR₁₀— in which
R₉ is hydrogen or methyl;
R₁₀ is hydrogen;
or an optical isomer thereof; or a mixture of optical isomers thereof; or a pharmaceutically acceptable salt thereof.

More preferred are the compounds of formula (IA) wherein
R, R' and R" are hydrogen;
Q is a bond; or
Q is —O(CH₂)$_r$— or —S(CH₂)$_r$— in which
r is zero; or
Q is —NR₇—, —NR₇C(O)—, —NR₇C(O)NR₈—or —NR₇C(O)O— in which
R₇ is hydrogen or optionally substituted lower alkyl;
W is cycloalkyl, aryl or heterocyclyl;
or an optical isomer thereof; or a mixture of optical isomers thereof; or a pharmaceutically acceptable salt thereof.

Most preferred are the compounds of formula (IA), wherein the asymmetric center in radical L is in the (R) configuration; or a pharmaceutically acceptable salt thereof.

Most preferred are also the compounds of formula (IA), wherein X₂ is —C(R₉)₂— in which R₉ is methyl; or an optical isomer thereof; or a mixture of optical isomers thereof; or a pharmaceutically acceptable salt thereof.

Most preferred are also the compounds of formula (IA) having the formula

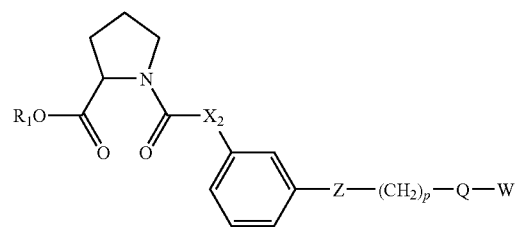

(IB)

wherein
R₁ is hydrogen or optionally substituted alkyl;
Z is a bond, O or S;
p is an integer from 1 to 3;
Q is a bond, O or S; or Q is —NR₇C(O)— in which
R₇ is hydrogen or optionally substituted lower alkyl;
W is aryl or heterocyclyl;
X₂ is —C(R₉)₂—, O, S or —NH— in which
R₉ is hydrogen or methyl;

or an optical isomer thereof; or a mixture of optical isomers thereof; or a pharmaceutically acceptable salt thereof.

Preferred are the compounds of formula (IB) wherein
Z is O or S;
p is an integer of 2 or 3;
Q is O or S;
W is selected from the group consisting of:

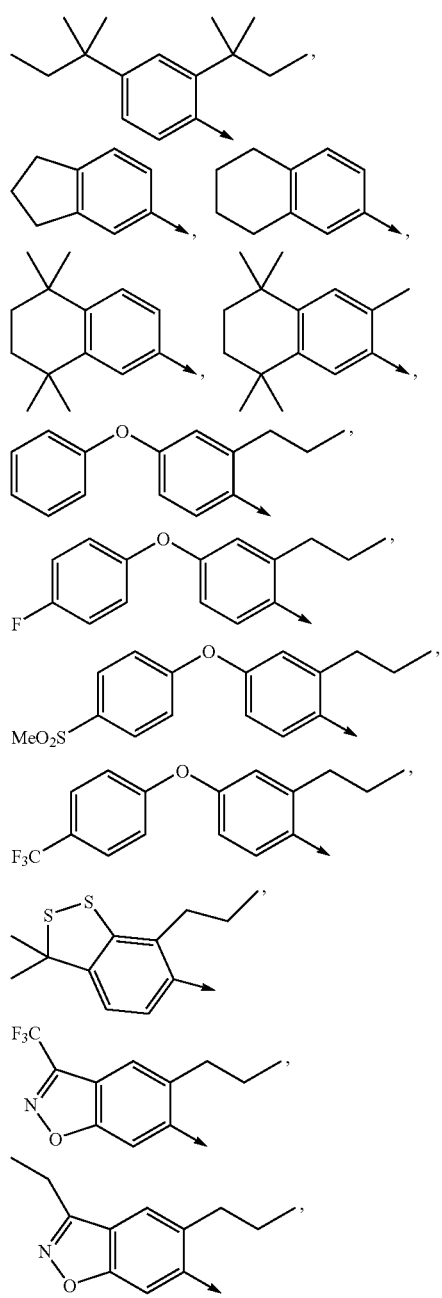

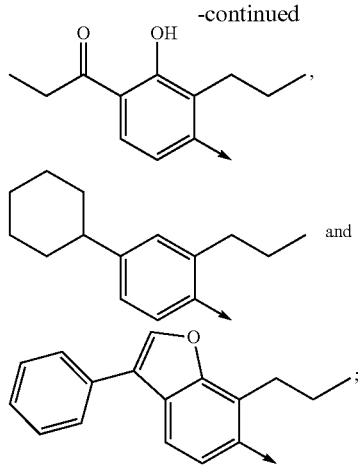

or an optical isomer thereof; or a mixture of optical isomers thereof; or a pharmaceutically acceptable salt thereof.

Preferred are also the compounds of formula (IB), designated as the A group, wherein
Z is bond, O or S;
p is an integer of 1 or 2;
Q is a bond;
W is selected from the group consisting of:

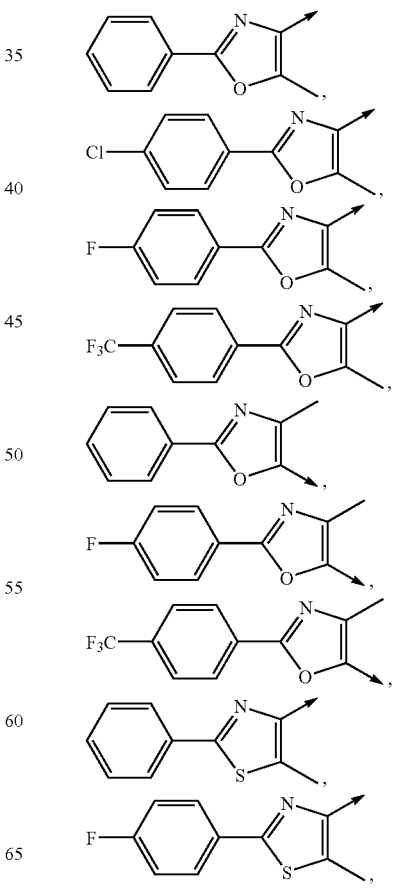

or an optical isomer thereof; or a mixture of optical isomers thereof; or a pharmaceutically acceptable salt thereof.

Preferred are the compounds in the A group wherein
Z is O;
p is 1;
$X_2$ is —$C(R_9)_2$— in which $R_9$ is methyl;
W is selected from the group consisting of:

or an optical isomer thereof; or a mixture of optical isomers thereof; or a pharmaceutically acceptable salt thereof.

Further preferred are the compounds in the A group wherein the asymmetric center in radical L is in the (R) configuration; or a pharmaceutically acceptable salt thereof.

Preferred are also the compounds of formula (IB) wherein
Z is O or S;
p is 2;
Q is a bond;
W is selected from the group consisting of:

-continued

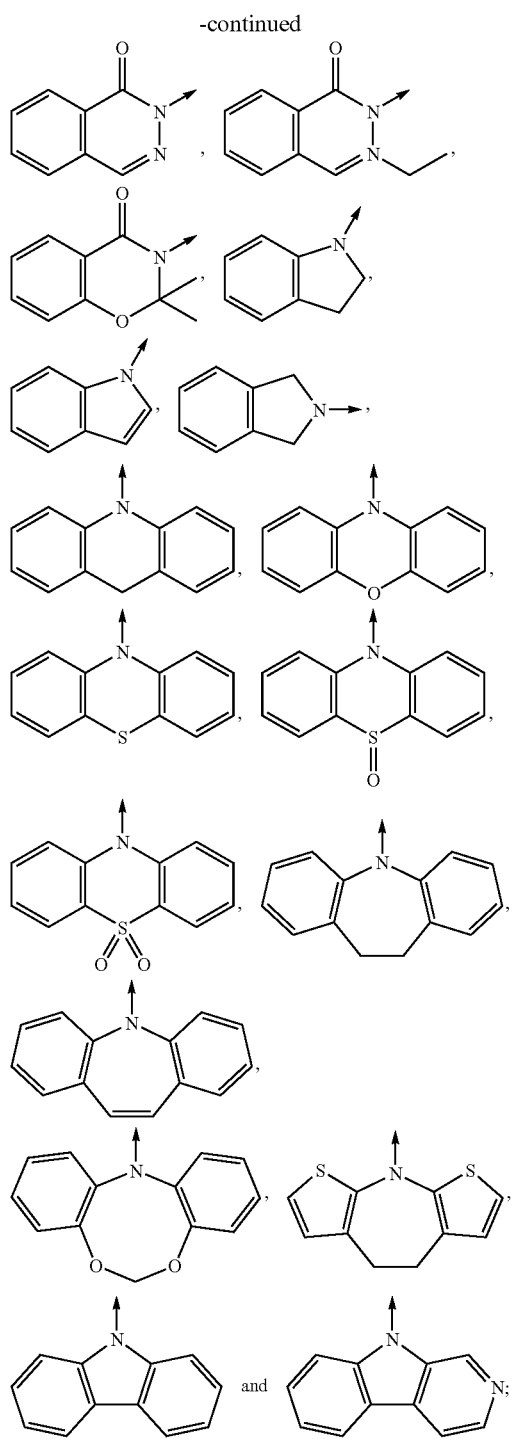

or an optical isomer thereof; or a mixture of optical isomers thereof; or a pharmaceutically acceptable salt thereof.

Preferred are also the compounds of formula (IB) wherein

Z is a bond;

p is 1;

Q is —NR$_7$C(O)— in which

R$_7$ is hydrogen or methyl;

W is selected from the group consisting of:

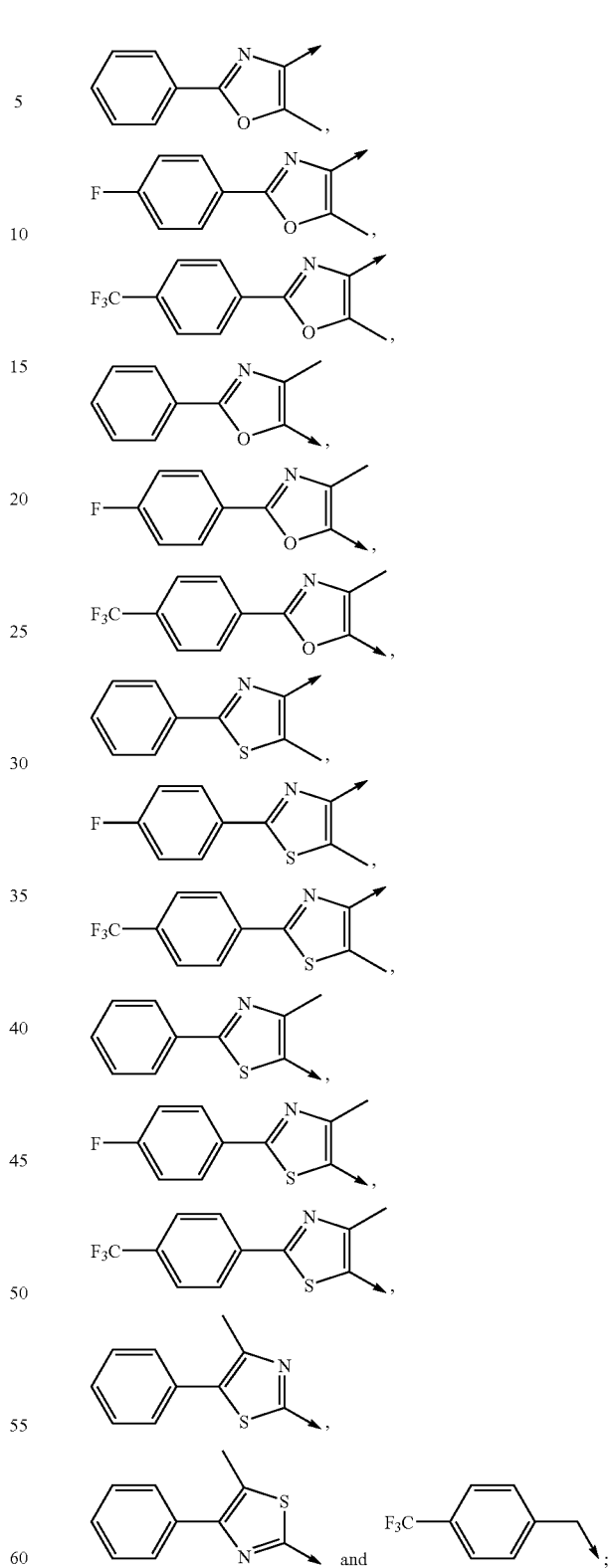

or an optical isomer thereof; or a mixture of optical isomers thereof; or a pharmaceutically acceptable salt thereof.

Most preferred are also the compounds of formula (IA) having the formula

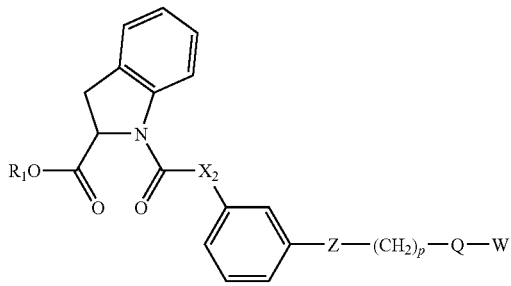

(IC)

wherein
R₁ is hydrogen or optionally substituted alkyl;
Z is a bond, O or S;
p is an integer from 1 to 3;
Q is a bond, O or S; or
Q is —NR₇C(O)— in which
R₇ is hydrogen or optionally substituted lower alkyl;
W is aryl or heterocyclyl;
X₂ is —C(R₉)₂—, O, S or —NH— in which
R₉ is hydrogen or methyl;

or an optical isomer thereof; or a mixture of optical isomers thereof; or a pharmaceutically acceptable salt thereof.

Preferred are the compounds of formula (IC) wherein
Z is O or S;
p is an integer of 2 or 3;
Q is O or S;
W is selected from the group consisting of:

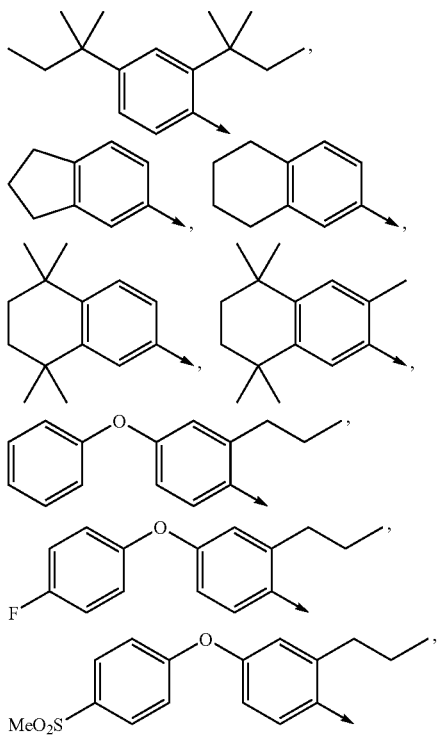

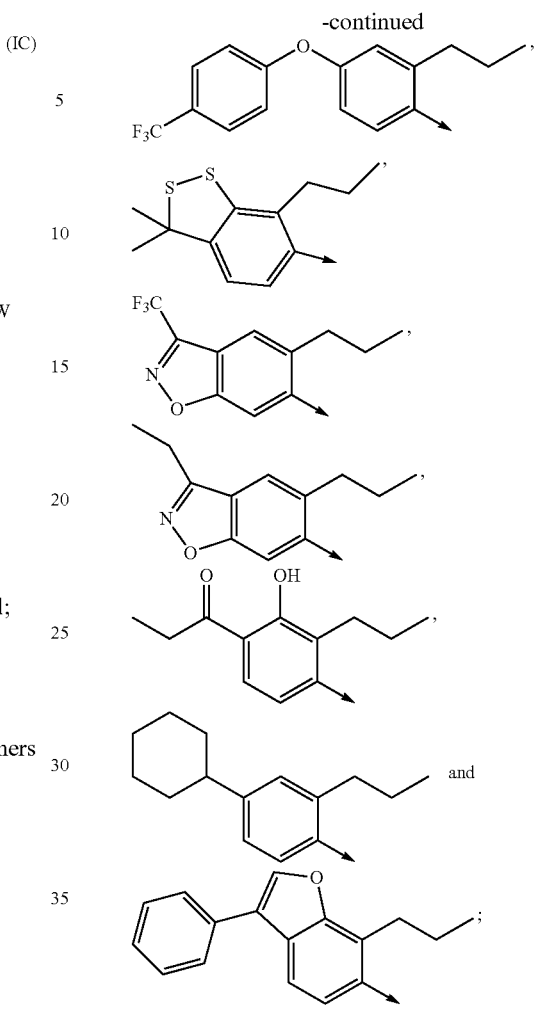

or an optical isomer thereof; or a mixture of optical isomers thereof; or a pharmaceutically acceptable salt thereof.

Preferred are also the compounds of formula (IC), designated as the B group, wherein
Z is bond, O or S;
p is an integer of 1 or 2;
Q is a bond;
W is selected from the group consisting of:

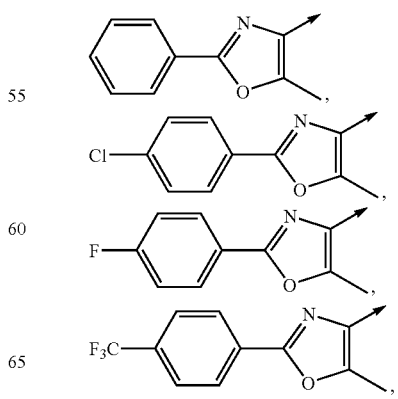

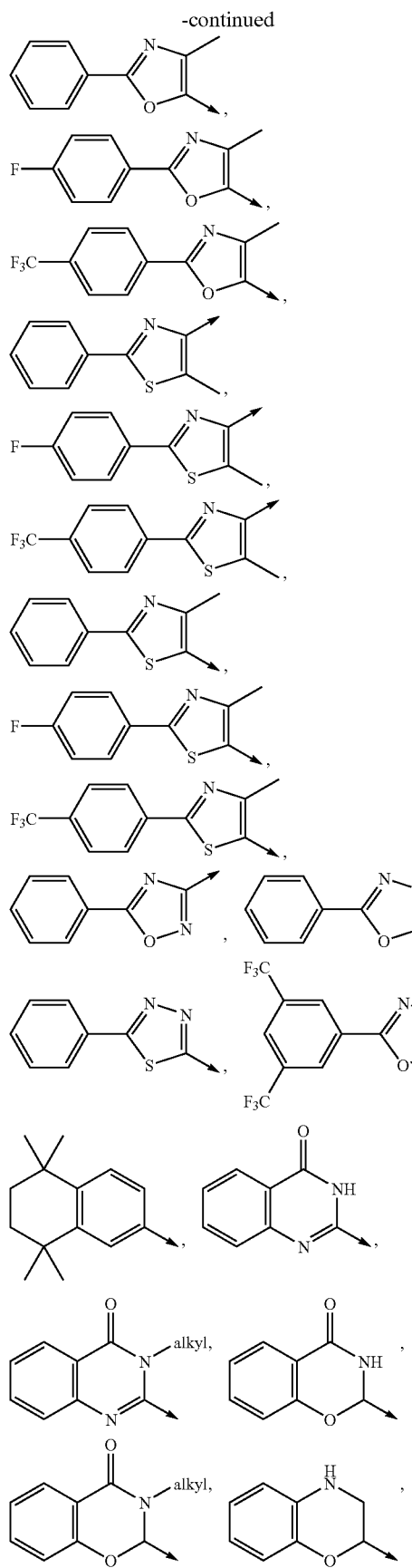

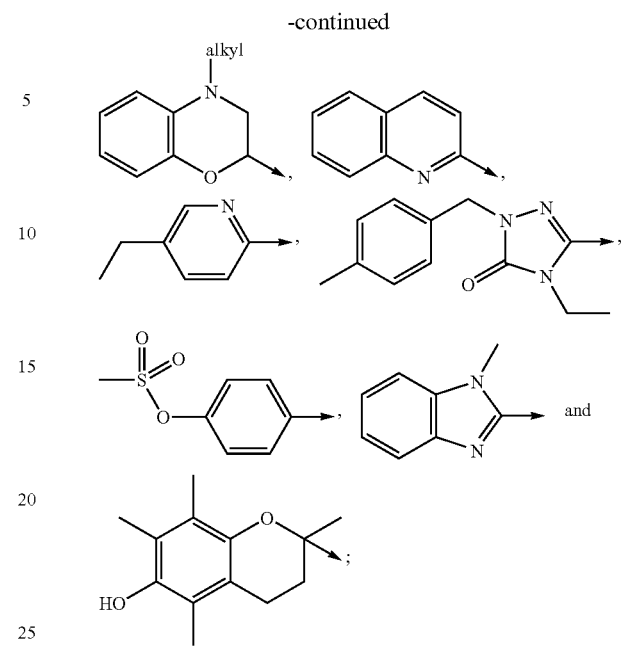

or an optical isomer thereof; or a mixture of optical isomers thereof; or a pharmaceutically acceptable salt thereof.

Preferred are the compounds in the B group wherein

Z is O;

p is 1;

$X_2$ is —$C(R_9)_2$— in which $R_9$ is methyl;

W is selected from the group consisting of:

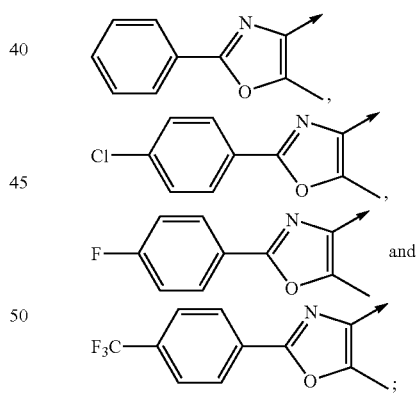

or an optical isomer thereof; or a mixture of optical isomers thereof; or a pharmaceutically acceptable salt thereof.

Further preferred are the compounds in the B group wherein the asymmetric center in radical L is in the (R) configuration; or a pharmaceutically acceptable salt thereof.

Preferred are also the compounds of formula (IC) wherein

Z is O or S;

p is 2;

Q is a bond;

W is selected from the group consisting of:

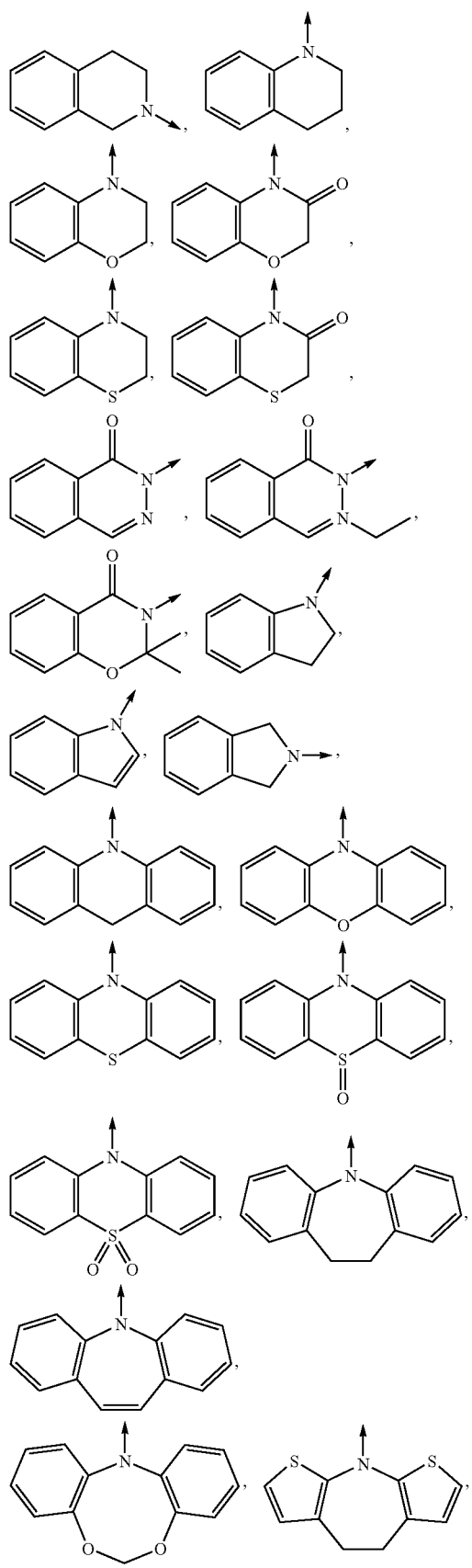
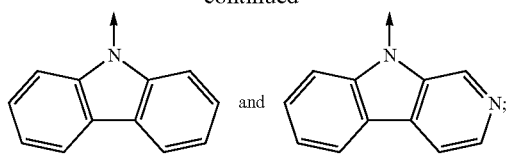
or an optical isomer thereof; or a mixture of optical isomers thereof; or a pharmaceutically acceptable salt thereof.
Preferred are also the compounds of formula (IC) wherein
Z is a bond;
p is 1;
Q is —NR$_7$C(O)— in which
R$_7$ is hydrogen or methyl;
W is selected from the group consisting of:
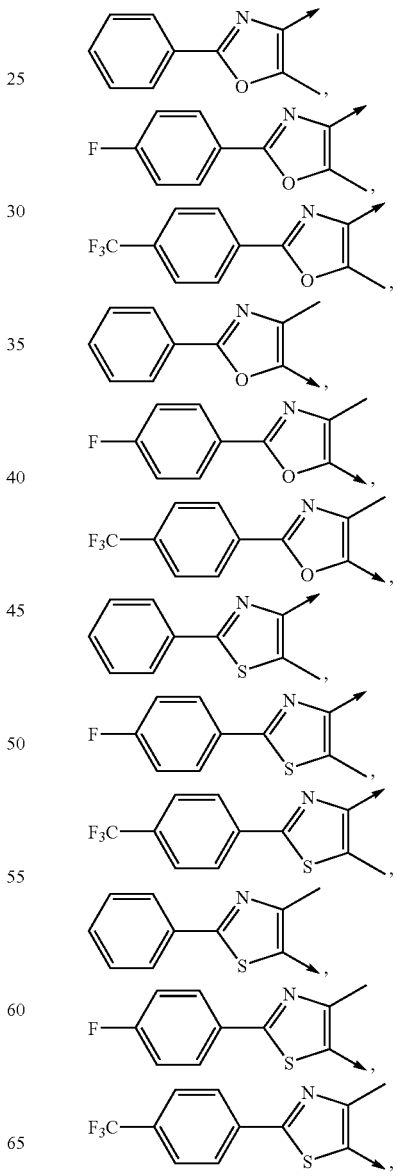

-continued

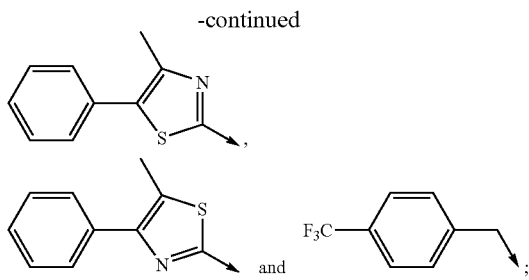

or an optical isomer thereof; or a mixture of optical isomers thereof; or a pharmaceutically acceptable salt thereof.

Particular embodiments of the invention are:

(R)-1-{2-[3-(5-Methyl-2-phenyl-oxazol-4-ylmethoxy)-phenyl]-acetyl}-pyrrolidine-2-carboxylic acid;
(R)-1-[3-(5-Methyl-2-phenyl-oxazol-4-ylmethoxy)-phenyl-sulfanylcarbonyl]-pyrrolidine-2-carboxylic acid;
(R)-Pyrrolidine-1,2-dicarboxylic acid-1-[3-(5-methyl-2-phenyl-oxazol-4-ylmethoxy)-phenyl]ester;
(R)-1-{2-Methyl-[2-(3-(5-methyl-2-phenyl-oxazol-4-ylmethoxy)-phenyl]-propionyl}-pyrrolidine-2-carboxylic acid;
(R)-1-{2-[4-(5-Methyl-2-phenyl-oxazol-4-ylmethoxy)-phenyl]-acetyl}-pyrrolidine-2-carboxylic acid;
(R)-1-{2-[4-(5-Methyl-2-phenyl-oxazol-4-ylmethoxy)-phenyl]-acetyl}-pyrrolidine-2-carboxylic acid;
(R)-1-(2-{3-[2-(4-Carbamoylphenyl)-5-methyl-oxazol-4-ylmethoxy]-phenyl}-2-methyl-propionyl)-pyrrolidine-2-carboxylic acid;
(R)-1-(2-{3-[2-(4-Cyano-phenyl)-5-methyl-oxazol-4-ylmethoxy]phenyl}-2-methyl-propionyl)-pyrrolidine-2-carboxylic acid;
(R)-1-(2-{3-[2-(4-Chloro-3-fluoro-phenyl)-5-methyl-oxazolyl-methoxy]-phenyl}-2-methyl-propionyl)-pyrrolidine-2-carboxylic acid;
(R)-1-(2-Methyl-2-[4-({methyl-[2-(4-trifluoromethyl-phenyl)-acetyl]-amino)methyl]-phenyl]-propionyl}-pyrrolidine-2-carboxylic acid;
(R)-1-(2-{3-[2-(4-Fluoro-phenyl)-5-methyl-oxazol-4-ylmethoxy]-4-methoxy-phenyl}-2-methyl-propionyl)-pyrrolidine-2-carboxylic acid;
(R)-1-(2-{3-[2-(4-Chloro-phenyl)-5-methyl-oxazol-4-ylmethoxy]-phenyl}-2-methyl-propionyl)-pyrrolidine-2-carboxylic acid;
(R)-1-2-Methyl-{2-[3-(5-methyl-2-p-olyi-oxazol-4-ylmethoxy)-phenyl]-propionyl}-pyrrolidine-2-carboxylic acid;
(R)-1-[2-(4-{2-[2-(4-Trifluoromethyl-phenyl)-acetylamino]-ethyl}-phenyl)-acetyl]-pyrrolidine-2-carboxylic acid;
(R)-1-(2-Methyl-2-{3-[5-methyl-2-(4-trifluoromethyl-phenyl)-oxazol-4-ylmethoxy]-phenyl}-propionyl)-pyrrolidine-2-carboxylic acid;
(R)-1-(2-{3-[2-(4-Fluoro-phenyl)-5-methyl-oxazol-4-ylmethoxy]-phenyl}-2-methyl-propionyl)-pyrrolidine-2-carboxylic acid;
(R)1-(2-{3-[2-(5-Methyl-2-phenyl-oxazol-4-yl)ethyl]-phenyl}-acetyl)-pyrrolidine-2-carboxylic acid;
(R)-1-[2-(3-{[(4-Methyl-5-phenyl-thiazole-2-carbonyl)-amino]-methyl}-phenyl)-acetyl]-pyrrolidine-2-carboxylic acid;
(R)1-[2-Methyl-2-(3-{[(4-methyl-2-phenyl-thiazole-5-carbonyl)-amino]-methyl}-phenyl)-propionyl]-pyrrolidine-2-carboxylic acid;
(R)-1-[2-(3-{[(4-Methyl-2-phenyl-thiazole-5-carbonyl)-amino]-methyl}-phenyl)-acetyl]-pyrrolidine-2-carboxylic acid;
(R)-1-{2-[3-(1-Benzyl-4-ethyl-5-oxo4,5-dihydro-1 H-[1,2,4]triazol-3-ylmethoxy)-phenyl]-acetyl}-pyrrolidine-2-carboxylic acid;
(R)-1-(2-{3-[2-(5-Methyl-2-phenyl-oxazol-4-yl)-ethoxy]-phenyl}-acetyl)-pyrrolidine-2-carboxylic acid;
(R)-1-(2-{3-[5-Methyl-2-(4-trifluoromethyl-phenyl)-oxazol-4-ylmethoxy]-phenyl}-acetyl)-pyrrolidine-2-carboxylic acid;
(S)-1-{2-[3-(5-Methyl-2-phenyl-oxazol-4-ylmethoxy)-phenyl]-acetyl}-pyrrolidine-2-carboxylic acid;
(R)-1-{2-[3-(4-Methyl-benzyloxy)-phenyl]-acetyl}-pyrrolidine-2-carboxylic acid;
(R)-1-{2-Methyl-2-[3-(5-methyl-2-phenyl-oxazol-4-ylmethoxy)-phenyl]-propionyl}-2,3-dihydro-1H-indole-2-carboxylic acid;
(R)-1-(2-{3-[2-(4-Carbamoyl-phenyl)-5-methyl-oxazol-4-ylmethoxy]-phenyl}-2-methyl-propionyl)-2,3-dihydro-1H-indole-2-carboxylic acid;
(R)-1-(2-{3-[2-(4-Chloro-3-fluoro-phenyl)-5-methyl-oxazol-4-ylmethoxy]-phenyl}-2-methyl-propionyl)-2,3-dihydro-1 H-indole-2-carboxylic acid;
(R)-1-(2-{3-[2-(4-Cyano-phenyl)-5-methyl-oxazol-4-ylmethoxy]-phenyl}-2-methyl-propionyl)-2,3-dihydro-1H-indole-2-carboxylic acid;
(R)-1-(2-{3-[2-(4-Fluoro-phenyl)-5-methyl-oxazol-4-ylmethoxy]-4-methoxy-phenyl}-2-methyl-propionyl)-2,3-dihydro-1H-indole-2-carboxylic acid;
(R)-1-{2-Methyl-2-[3-(5-methyl-2-p-tolyl-oxazol-4-ylmethoxy)-phenyl]-propionyl}-2,3-dihydro-1H-indole-2-carboxylic acid;
(R)-1-(2-Methyl-2-{3-[5-methyl-2-(4-trifluoromethyl-phenyl)-oxazol-4-ylmethoxy]-phenyl}-propionyl)-2,3-dihydro-1H-indole-2-carboxylic acid;
(R)-1-(2-{3-[2-(4-Chloro-phenyl)-5-methyl-oxazol-4-ylmethoxy]-phenyl}-2-methyl-propionyl)-2,3-dihydro-1H-indole-2-carboxylic acid; and
(R)-1-(2-{3-[2-(4-Fluoro-phenyl)-5-methyl-oxazol-4-ylmethoxy]-phenyl}-2-methyl-propionyl)-2,3-dihydro-1H-indole-2-carboxylic acid;

or an optical isomer thereof; or a mixture of optical isomers thereof; or a pharmaceutically acceptable salt thereof.

Compounds of formula (I) wherein $X_2$ represents —$C(R_9)_2$— in which $R_9$ has a meaning as defined herein may be prepared by reacting an activated derivative of a carboxylic acid of the formula (IV)

wherein R and R' have meanings as defined herein, $X_1'$ represents $X_1$ as defined herein, or $X_1'$ is a groups convertible to $X_1$, and $X_2$ represents —$C(R_9)_2$— in which $R_9$ has a meaning as defined herein, with an amine of the formula

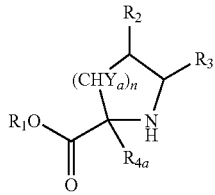
(II')

or

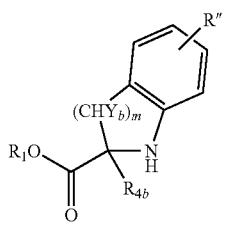
(III')

in which $R_1$, $R_2$, $R_3$, $R_{4a}$, $Y_a$, n, R", $R_{4b}$, $Y_b$ and m have meanings as defined herein, to afford compounds of the formula

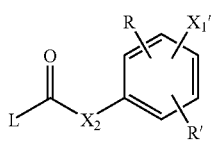
(I')

wherein R, R', $X_1'$ and $X_2$ have meanings as defined for formula (IV), and L is a radical selected from the group consisting of:

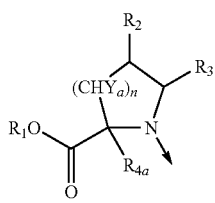
(II)

and

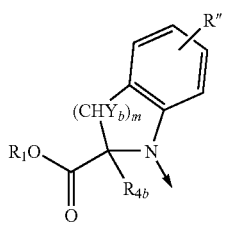
(III)

in which $R_1$, $R_2$, $R_3$, $R_{4a}$, $Y_a$, n, R", $R_{4b}$, $Y_b$ and m have meanings as defined herein above. Amines of formula (II') and (III') may be obtained by methods described herein or modifications thereof, or by methods generally known in the art.

In the processes cited herein, activated derivatives of carboxylic acids, e.g., those corresponding to carboxylic acids of formula (IV), include acid chlorides, bromides and fluorides, mixed anhydrides, lower alkyl esters and activated esters thereof, and adducts formed with coupling agents, such as 1-ethyl-3-(3-dimethylaminopropyl)carbodiimide hydrochloride (EDCl), O-(1,2-dihydro-2-oxo-1-pyridyl)-N,N,N',N'-tetramethyluronium tetrafluoroborate and the like. Mixed anhydrides are preferably such from pivalic add, or lower alkyl hemiesters of carbonic acids, such as ethyl or isobutyl analogs. Activated esters include, for example, succinimido, phthalimido or 4-nitrophenyl esters. The reaction of an activated derivative of a carboxylic acid, e.g., those corresponding to carboxylic acids of formula (IV), with an amine, e.g., those of formula (II') and (III'), may be carried out in the presence of a base, such as triethylamine (TEA), diisopropylethylamine (DIEA) or N-methylmorpholine (NMM) in an inert organic solvent, such as dichloromethane (DCM), N,N-dimethylformamide (DMF) or tetrahydrofuran (THF). Carboxylic acids of formula (IV) can be converted to their activated derivatives using methods described herein or according to methods generally known in the art.

Compounds of formula (I) wherein $X_2$ is O, S or —$NR_{10}$— in which $R_{10}$ has a meaning as defined herein may be prepared, e.g., by first converting amines of formula (II') or (III') to carbamoyl chlorides of the formula

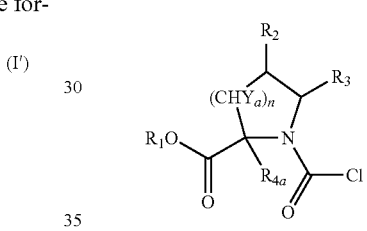
(V)

or

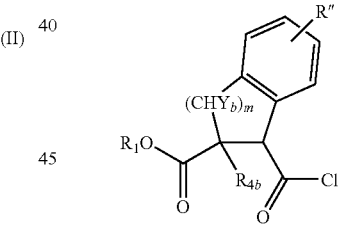
(VI)

wherein $R_1$, $R_2$, $R_3$, $R_{4a}$, $Y_a$, n, R", $R_{4b}$, $Y_b$ and m have meanings as defined herein, by treatment with a reagent such as phosgene, or analogs thereof, in the presence of a base, such as TEA, DIEA or NMM, in an inert solvent such DCM, DMF or THF.

Carbamoyl chlorides of formula (V) or (VI) may then be reacted with a compound of the formula

(VII)

wherein R and R' have meanings as defined herein, $X_1'$ represents $X_1$ as defined herein, or $X_1'$ is a groups convertible to $X_1$, and $X_2$ is O, S or —$NR_{10}$— in which $R_{10}$ has a meaning as defined herein, in the presence of a base, such as potassium or cesium carbonate, in an organic solvent, such as THF or DMF, to afford compounds of formula (I') wherein $X_2$ is O, S or —$NR_{10}$— in which $R_{10}$ has a meaning as defined herein.

Compounds of formula (I') wherein $X_1'$ represents $X_1$ as defined herein can be obtained from compounds of formula (I') wherein $X_1'$ is a group convertible to $X_1$ using methods described herein or modifications thereof, or using methods well known in the art. For example, compounds of the formula

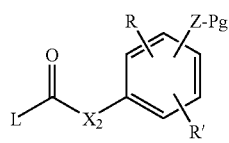

(Ia')

wherein R, R', $X_2$ and L have meanings as defined herein, Z is O or S, and Pg represents a protecting group, such as benzyl, trialkylsilyl, e.g., t-butyldimethylsilyl, or acyl, may be converted to compounds of the formula

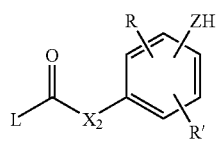

(Ib')

wherein R, R', $X_2$, L and Z have meanings as defined for formula (Ia'), according to methods described herein in the illustrative Examples or using conditions generally known in the art.

Compounds of formula (Ib') may then be treated with an alkylating agent of the formula

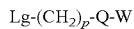  (VIII)

wherein p, Q and W have meanings as defined herein and Lg represents a leaving group, such as iodide, bromide, chloride or trifluoromethanesulfonate, in the presence of a base, such as potassium or cesium carbonate, in an inert solvent, such as THF or DMF, to form compounds of formula (I') wherein $X_1'$ is -Z-$(CH_2)_p$-Q-W in which Z is O or S, and p, Q and W have meanings as defined herein.

Preferably, the alkylating agent of formula (VIII) is selected from a group wherein p is an integer of 2 or 3, Q is O or S, Lg is chloride or bromide and W is

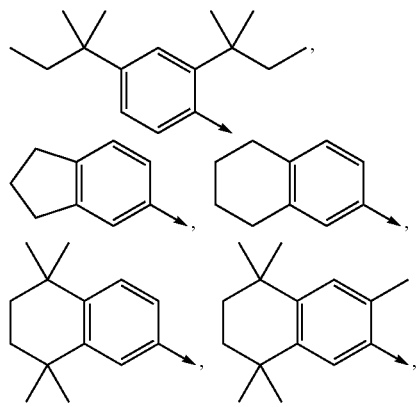

-continued

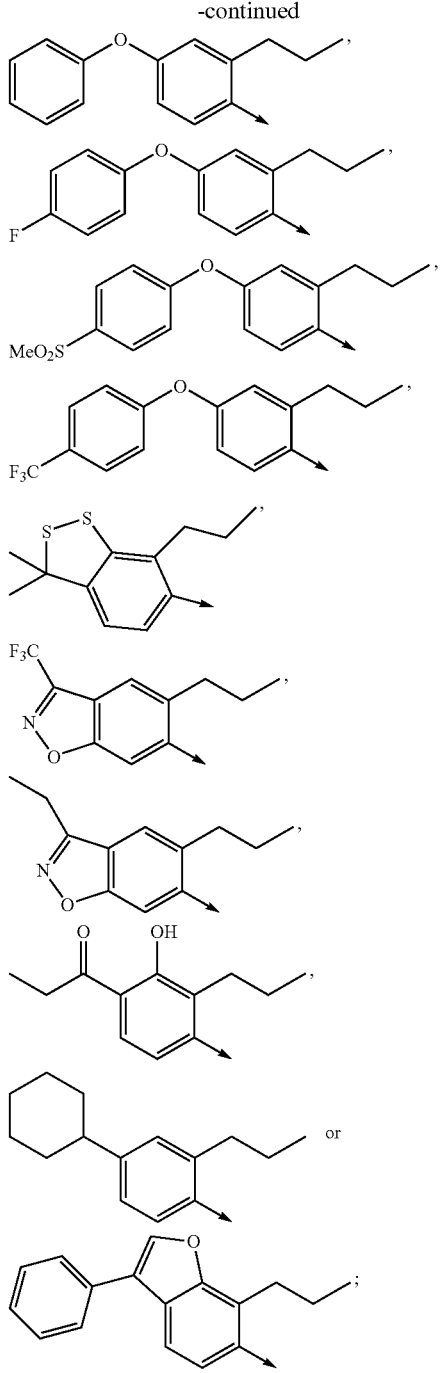

or the alkylating agent of formula (VIII) is selected from a group wherein p is 1 or 2, Q is a bond, Lg is chloride or bromide and W is

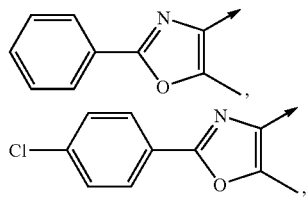

-continued
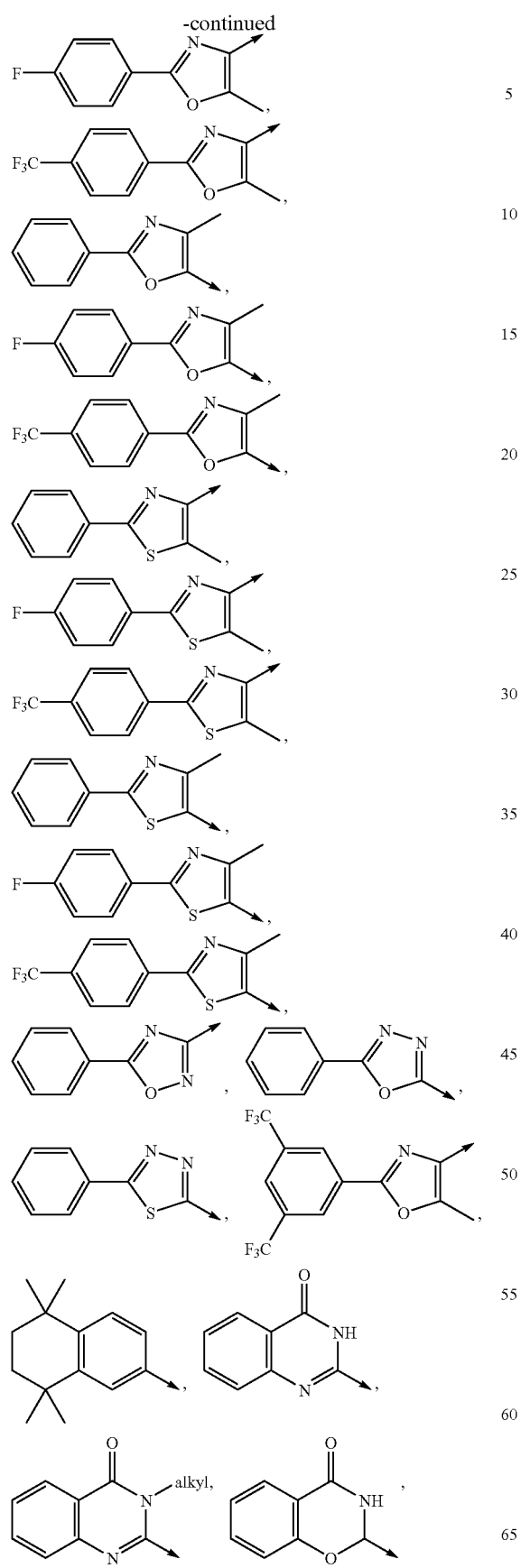
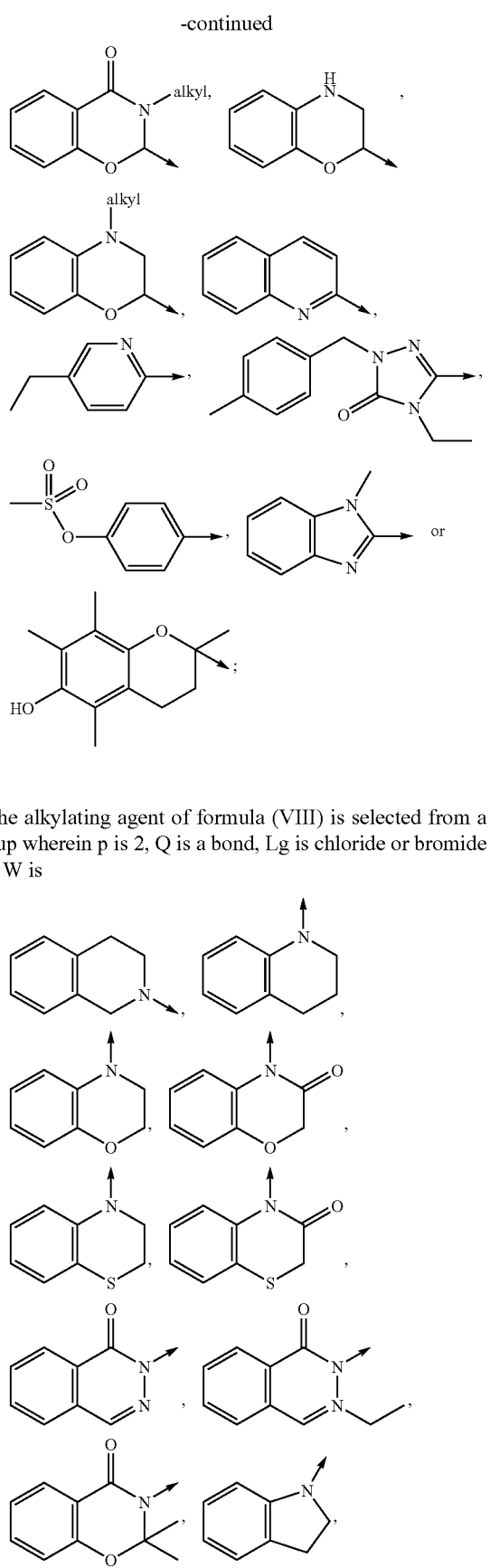
or the alkylating agent of formula (VIII) is selected from a group wherein p is 2, Q is a bond, Lg is chloride or bromide and W is -continued

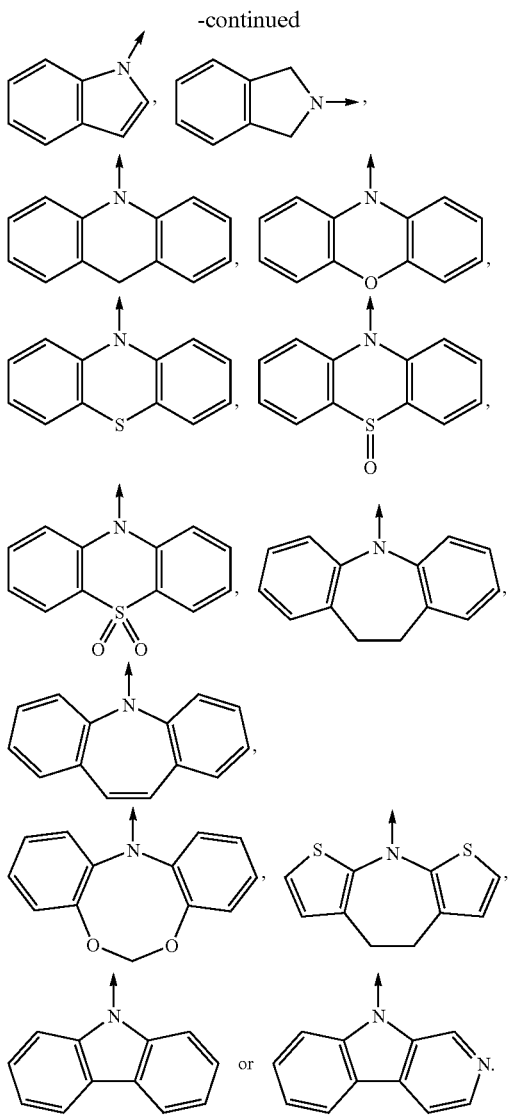

The alkylating agents of formula (VIII) may be prepared using methods described herein or modifications thereof, or using methods known in the art, e.g., 4-chloromethyl-5-methyl-2-phenyloxazole and 4-chloromethyl-5-methyl-2-[4-(trifluoromethyl)-phenyl]-oxazole may be prepared using methods described in International PCT Patent Application No. WO 00/64888 or according to *J. Med. Chem.*, Vol. 43, pp. 995-1010 (2000). 1-(3-Bromo-propoxy)-4-phenoxy-2-propyl-benzene may be prepared as described in International PCT Patent Application No. WO 00/78312.

Preferably, alkylating agents of formula (VIII) having the formula (VIIIa)

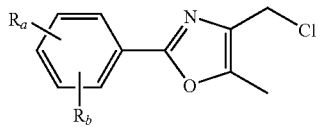

wherein $R_a$ and $R_b$ are independently hydrogen, halogen, alkyl, alkoxy, trifluoromethyl or aryl, may be prepared by treating a compound of the formula (VIIIb)

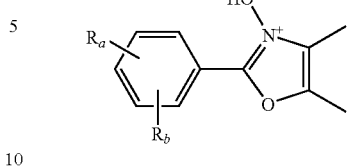

wherein $R_a$ and $R_b$ have meanings as defined for formula (VIIIa), with a chlorinating agent, such as phosphorus oxychloride ($POCl_3$), in acetonitrile. It is essential that the reaction is carried out in acetonitrile in order to obtain alkylating agents of formula (VIIIa) in high chemical yield and purity, i.e., the alkylating agents of formula (VIIIa) are obtained according to the present method in high regioselectivity, preferably in greater than 99% selectivity. The chlorination is preferably conducted at an ambient temperature, e.g. at room temperature (RT).

Compounds of formula (VIIIb) may be prepared by condensing an aldehyde of the formula (VIIIc)

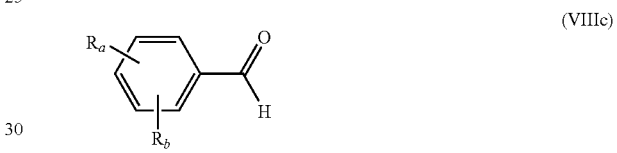

wherein $R_a$ and $R_b$ have meanings as defined for formula (VIIIa), with 2,3-butadione monooxime of the formula (VIIId)

in the presence of an acid catalyst, such as gaseous hydrochloric acid and an organic solvent, such as ethyl acetate or acetic acid, preferably glacial acetic acid, to afford compounds of formula (VIIIb) wherein $R_a$ and $R_b$ have meanings as defined herein above.

Alternatively, compounds of formula (Ib') may be treated with an alcohol of the formula

 (VIII')

wherein p, Q and W have meanings defined herein, under Mitsunobu conditions, e.g., in the presence of triphenylphoshine and diethyl azodicarboxylate in an organic solvent, such as THF, to afford compounds of formula (I') wherein $X_1'$ is -Z-$(CH_2)_p$-Q-W in which Z is O or S, and p, Q and W have meanings as defined herein. Alcohols of formula (VIII″) may be prepared by methods described herein or modifications thereof, or by methods well known in the art.

Compounds of formula (I') wherein $X_1'$ is -Z-$(CH_2)_p$-Q-W in which Z is a bond, p and W have meanings as defined herein, and Q represents O or S, may be obtained, e.g., by treating compounds of the formula

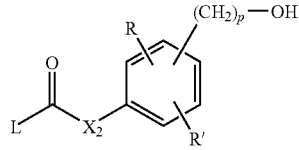

wherein R, R', p, $X_2$ and L have meanings as defined herein, with phenols of formula W—OH or thiols of formula W—SH, e.g., under Mitsunobu conditions, to form compounds of formula (I') wherein R, R', $X_2$ and L have meanings as defined herein, and $X_1'$ represents -Z-$(CH_2)_p$-Q-W, in which Z is a bond, p and W have meanings as defined herein, and Q is O or S, respectively. Compounds of formula (IX) may be prepared by methods described herein or modifications thereof, or by methods generally known in the art.

Alternatively, alcohols of formula (IX) may be converted to compounds of the formula

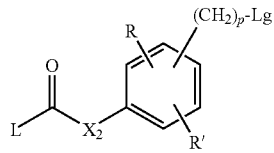

wherein R, R', p, $X_2$ and L have meanings as defined herein and Lg represents a leaving group, such as iodide, chloride, bromide or trifluorosulfonate, using methods described herein or modifications thereof, or using methods well-known in the art. Subsequent reaction of compounds of formula (X) with a phenol of formula W—OH or a thiol of formula W—SH in the presence of a base, such as potassium or cesium carbonate, in an inert solvent, such as DMF or THF, affords compounds of formula (I') wherein R, R', $X_2$ and L have meanings as defined herein, and $X_1'$ represents -Z-$(CH_2)_p$-Q-W, in which Z is a bond, p and W have meanings as defined herein, and Q is O or S, respectively.

Compounds of formula (I') wherein R, R', $X_2$ and L have meanings as defined herein, and $X_1'$ represents -Z-$(CH_2)_p$-Q-W in which Z is —C(O)$NR_5$— and $R_5$, p, Q and W have meanings as defined herein, may be prepared by reacting an activated derivative of a carboxylic acid corresponding to a carboxylic acid of the formula

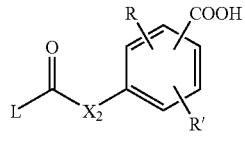

wherein R, R', $X_2$ and L have meanings as defined herein, with amines, or acid addition salts thereof, of the formula

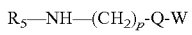

wherein $R_5$, p, Q and W have meanings as defined herein. Carboxylic acids of formula (XI) and amines of formula (XII) may be prepared using methods described herein or modifications thereof, or using methods generally known in the art.

Similarly, compounds of formula (I') wherein R, R', $X_2$ and L have meanings as defined herein, and $X_1'$ represents -Z-$(CH_2)_p$-Q-W wherein Z, p and W have meanings as defined herein, and Q is —C(O)$NR_6$— in which $R_6$ has a meaning as defined herein, may be prepared by reacting an activated derivative of a carboxylic acid corresponding to a carboxylic acid of the formula

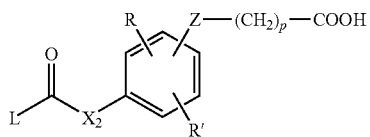

wherein R, R', $X_2$, L, Z and p have meanings as defined herein, with amines, or acid addition salts thereof, of the formula

wherein $R_6$ and W have meanings as defined herein above. Carboxylic acids of formula (XIII) and amines of formula (XIV) may be prepared using methods described herein or modifications thereof, or using methods known in the art.

Compounds of formula (I') wherein R, R', $X_2$ and L have meanings as defined herein, and $X_1'$ represents -Z-$(CH_2)_p$-Q-W wherein Z, p and W have meanings as defined herein, and Q is —$NR_7$C(O)—, —$NR_7$C(O)$NR_8$— or —$NR_7$C(O)O— in which $R_7$ and $R_8$ have meanings as defined herein, may be obtained by reacting amines of the formula

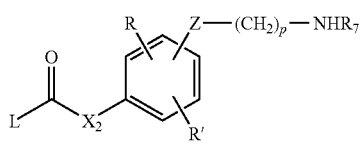

wherein R, R', $X_2$, L, Z, p and $R_7$ have meanings as defined herein, with a N-derivatizing agent, such as an activated derivative of a carboxylic acid,. an isocyanate or a chloroformate, respectively, in the presence of a base, such as TEA, DIEA or NMM, in an inert solvent, such as DCM, DMF or THF. Amines of formula (XV) may be prepared using methods described herein or modifications thereof, or using methods generally known in the art.

Preferably, the N-derivatizing agent is an activated derivative of a carboxylic acid of the formula

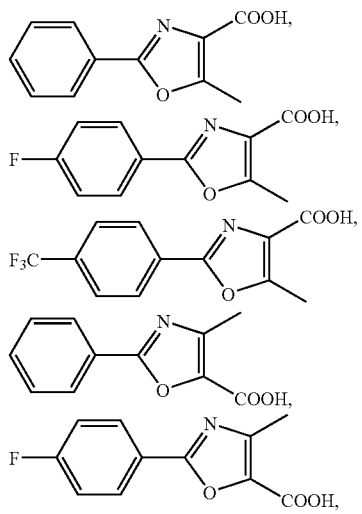

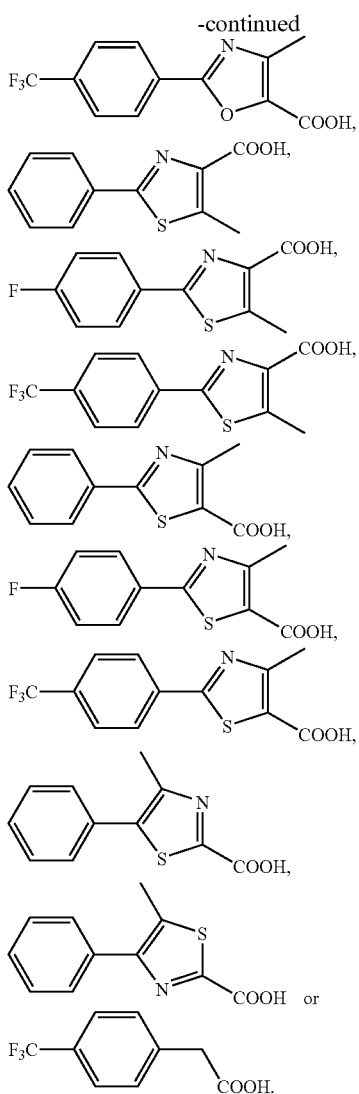

Compounds of formula (I') in which R, R', $X_2$, L and $X_1$' have meanings as defined herein, and $R_1$ is optionally substituted alkyl, aryl, heteroaryl, aralkyl or cycloalkyl can be converted to compounds of the formula (I') in which RI is hydrogen using reaction conditions described herein or modifications thereof, or using methods know in the art, e.g., compounds of formula (I') in which $R_1$ is lower alkyl, such as methyl or ethyl, may be treated with an aqueous base, such as sodium, lithium or potassium hydroxide, in a polar solvent, such as methanol, ethanol, 1,4-dioxane or THF, to afford compounds of formula (I') in which R, R', $X_2$, L and $X_1$' have meanings as defined herein, and $R_1$ is hydrogen.

The starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxy groups are those that can be converted under mild conditions into free amino, thiol, carboxyl and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, RT or elevated temperatures (preferably at or near the boiling point of the solvents used), and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials and processes for their manufacture.

Depending on the choice of starting materials and methods, the compounds may be in the form of one of the possible isomers or mixtures thereof, for example, as substantially pure geometric (cis or trans) isomers, optical isomers (antipodes), racemates or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example, by chromatography and/or fractional crystallization.

Any resulting racemates of final products or intermediates can be resolved into the optical antipodes by known methods, e.g., by separation of the diastereoisomeric salts thereof, obtained with an optically active acid or base, and liberating the optically active acidic or basic compound. The carboxylic acid intermediates can thus be resolved into their optical antipodes, e.g., by fractional crystallization of D- or L-(alpha-methylbenzylamine, cinchonidine, cinchonine, quinine, quinidine, ephedrine, dehydroabietylamine, brucine or strychnine)-salts. Racemic products can also be resolved by chiral chromatography, e.g., high pressure liquid chromatography using a chiral adsorbent.

Finally, compounds of the invention are either obtained in the free form, or as a salt thereof if salt forming groups are present.

Acidic compounds of the invention may be converted into salts with pharmaceutically acceptable bases, e.g., an aqueous alkali metal hydroxide, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example, sulfuric acid, a phosphoric or hydrohalic acid; or with organic carboxylic acids, such as ($C_1$-$C_4$)-alkanecarboxylic acids which, for example, are unsubstituted or substituted by halogen, for example, acetic acid, such as saturated or unsaturated dicarboxylic acids, for example, oxalic, succinic, maleic or fumaric acid, such as hydroxy-carboxylic acids, for example, glycolic, lactic, malic, tartaric or citric acid, such as amino acids, for example, aspartic or glutamic acid; or with organic sulfonic acids, such as ($C_1$-$C_4$)-alkyl-sulfonic acids, for example, methanesulfonic acid; or arylsulfonic acids which are unsubstituted or substituted, for example, by halogen. Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal or parenteral administration to mammals, including man, for the treatment of conditions mediated by PPAR receptors, in particular, PPARα. Such conditions include dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X. The said pharmaceutical compositions comprise an effective amount of a pharmacologically active compound of the instant invention, alone or in combination with one or more pharmaceutically acceptable carriers.

The pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with: a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable compositions for transdermal application include a therapeutically effective amount of a compound of the invention with a carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The present invention provides pharmaceutical compositions comprising a therapeutically effective amount of a compound of the invention in combination with one or more pharmaceutically acceptable carriers.

Thus, the present invention provides pharmaceutical compositions as described above for the treatment of conditions mediated by PPARs, preferably, dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include insulin, insulin derivatives and mimetics; insulin secretagogues, such as the sulfonylureas, e.g., Glipizide, glyburide and Amaryl; insulinotropic sulfonylurea receptor ligands, such as meglitinides, e.g., nateglinide and repaglinide; insulin sensitizers, such as protein tyrosine phosphatase-1B (PTP-1B) inhibitors such as PTP-112; GSK3 (glycogen synthase kinase-3) inhibitors such as SB-517955, SB4195052, SB-216763, NN-57-05441, NN-57-05445 or RXR ligands such as GW-0791, AGN-194204; sodium-dependent glucose cotransporter inhibitors, such as T-1095; glycogen phosphorylase A inhibitors, such as BAY R3401; biguanides, such as metformin; alpha-glucosidase inhibitors, such as acarbose; GLP-1 (glucagon like peptide-1), GLP-1 analogs, such as Exendin4, and GLP-1 mimetics; DPPIV (dipeptidyl peptidase IV) inhibitors such as LAF237; hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin, squalene synthase inhibitors or FXR (farnesoid X receptor) and LXR (liver X receptor) ligands, cholestyramine, fibrates, nicotinic acid and aspirin; anti-obesity agents, such as orlistat; anti-hypertensive agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na-K-ATPase membrane pump, such as digoxin; neutralendopeptidase (NEP) inhibitors; ACE/NEP inhibitors, such as omapatrilat, sampatrilat and fasidotril; angiotensin 11 antagonists, such as candesartan, eprosartan, irbesartan, losartan, telmisartan and valsartan, in particular valsartan; β-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil; aldosterone receptor antagonists and aldosterone synthase inhibitors. Other specific antidiabetic compounds are described by Patel Mona in *Expert Opin Investig Drugs*, 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the active agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents, anti-hypertensive agents or inotropic agents, most preferably from antidiabetics or hypolipidemic agents as described above.

The present invention further relates to pharmaceutical compositions as described above for use as a medicament.

Thus, the present invention relates to use of pharmaceutical compositions or combinations as described above for the preparation of a medicament for the treatment of conditions mediated by PPARs, preferably, dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

A unit dosage for a mammal of about 50-70 kg may contain between about 1 mg and 1000 mg, advantageously between about 5-500 mg of the active ingredient. The therapeutically effective dosage of active compound is dependent on the species of warm-blooded animal (mammal), the body weight, age and individual condition, on the form of administration, and on the compound involved.

The compounds of the present invention bind to PPARs, and thus may be employed for the treatment of conditions mediated by the PPARs. Such compounds may therefore be employed therapeutically for the treatment of dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

Thus, the present invention also relates to a compound of formula (I) for use as a medicament; to the use of a compound of formula (I) for the preparation of a pharmaceutical composition for the prevention and/or treatment of conditions mediated by PPARs; and to a pharmaceutical composition for use in conditions mediated by PPARs comprising a compound of formula (I) in free form or pharmaceutically acceptable salt form in association with a pharmaceutically acceptable diluent or carrier therefore.

Furthermore, the present invention provides a method for the prevention and/or treatment of conditions mediated by PPARs, which comprises administering a therapeutically effective amount of a compound of the present invention.

In accordance with the foregoing the present invention also provides a therapeutic combination, e.g., a kit, kit of parts, e.g., for use in any method as defined herein, comprising a compound of formula (I), in free form or in pharmaceutically acceptable salt form, to be used concomitantly or in sequence with at least one pharmaceutical composition comprising at least another therapeutic agent, preferably selected from antidiabetics, hypolipidemic agents, anti-obesity agents, anti-hypertensive agents or inotropic agents. The kit may comprise instructions for its administration.

Similarly, the present invention provides a kit of parts comprising: (i) a pharmaceutical composition of the invention; and (ii) a pharmaceutical composition comprising a compound selected from an antidiabetic, anti-obesity agent, anti-hypertensive agent, inotropic agent or hypolipidemic agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula (I) in free form or in pharmaceutically acceptable salt form, and a second drug substance, said second drug substance being a antidiabetic, anti-obesity agent, anti-hypertensive agent, inotropic agent or hypolipidemic agent, e.g., as indicated above.

Preferably, a compound of the invention is administered to a mammal in need thereof.

Preferably, a compound of the invention is used for the treatment of a disease which responds to modulation of the PPAR activity, particularly, PPARα activity.

Preferably, the conditions associated with PPAR activity are selected from dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

Finally, the present invention provides a method or use which comprises administering a compound of formula (I) in combination with a therapeutically effective amount of an antidiabetic agent, anti-obesity agent, anti-hypertensive agent, inotropic agent or hypolipidemic agent.

Ultimately, the present invention provides a method or use which comprises administering a compound of formula (I) in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests, using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-5}$ molar and $10^{-10}$ molar concentrations. A therapeutically effective amount in vivo may range depending on the route of administration, between about 1 and 500 mg/kg, preferably between about 5 and 100 mg/kg.

The activity of a compound according to the invention can be assessed by the following methods or methods well-described in the art:

The in vitro functional binding to the PPARα, PPARδ and PPARγ receptors is determined as follows:

The functional binding assays for the PPARα, PPARδ and PPARγ receptors are a variation of the coactivator-dependent receptor ligand assay (CARLA) (see Krey et al., "Fatty Acids, Eicosanoids, and Hypolipidemic Agents Identified as Ligands of Peroxisome Proliferator-Activated Receptors by Coactivator-Dependent Receptor Ligand Assay", *Molecular Endocrinology*, Vol. 11, pp. 779-791 (1997)). The present CARLA assays use a TR-FRET detection method previously reviewed (see Hemmila, "LANCE: Homogeneous Assay Plafform for HTS", *J. Biomol. Screening*, Vol. 4, pp. 303-307 (1999); Mathis, "HTRF Technology", *J. Biomol. Screening*, Vol. 4, pp. 309-313 (1999)). All assays included 3 nM of the glutathione-S-transferase (GST) fusion proteins of either the hPPARα ligand binding domain (LBD) (amino acids 167-468) (GST-hPPARα LBD), GST-hPPARδ LBD (amino acids 139-442) or GST-hPPARγ LBD (amino acids 175-476); 3 nM Eu-labeled anti-GST antibody (Wallac); 30 nM biotinylated steroid receptor coactivator-1 (SRC-1) peptide (an N-terminal biotinylated peptide, CPSSHSSLTERHKILHRLLQEG-SPS, derived from amino acids 676-700 of SRC-1); and 10 nM streptavidin-labelled allophycocyanin (APC; Prozyme). The binding of a ligand to a PPAR LBD alters the conformation of the LBD and permits the biotinylated SRC-1 peptide to bind. This brings the Eu-labeled anti-GST antibody and the strepavidin-labeled APC in close proximity, thereby facilitating fluorescence energy transfer. The biotinylated SRC-1 peptide is prepared by standard solid-phase peptide synthetic methods. The GST-PPAR LBDs are expressed in pGEX vectors (Amersham Pharmacia) in the *E. coli* strain BL21(DE3) using standard expression conditions at 18° C. In some cases the GST-PPAR LBDs are co-expressed with groESL. The GST fusion proteins are purified on glutathione sepharose affinity columns (Amersham Pharmacia) using the method described by the manufacturer. The assay buffer contained 50 mM Tris pH 7.4, 50 mM KCl, 0.1% BSA and 1 mM DTT (dithiothreitol). The assay is carried out in black half area 96-well plates in a final volume of 25 μL. After mixing all components, the reaction mixture stands for 3 hours at RT before reading the TR-FRET (Time-Resolved Fluorescence Resonance Energy Transfer) signal on a Wallac Victor 2 plate reader (measuring the ratio of signals at 665 nM and 620 nM). $EC_{50}$ values are estimated with the Excel add-in program XLFit (ID Business Solutions, Guildford, Surrey, UK) utilizing a 4-parameter logistic equation.

The glucose and insulin lowering activity in vivo can be evaluated as follows:

Adult male C57BL ob/ob mice (Jackson Lab, Bar Harbor, Me.) at the age of 11 weeks are housed six per cage in a reversed light cycle room (light on from 6:00 p.m. to 6:00 a.m.) and given access to Purina rodent chow and water ad libitum. On day 1, tail blood samples are taken at 8:00 am and plasma glucose levels are determined. The animals are randomly assigned to the control and compound groups. The means of plasma glucose values of the groups were matched. Animals are then orally dosed with vehicle (0.5% carboxymethyl-cellulose with 0.2% Tween-80) or compounds (at 30 mg/kg) in vehicle. The mice are dosed daily for a total of 3 days. On day 4, basal blood samples are taken. The plasma samples are analyzed for glucose concentrations using a YSI2700 Dual Channel Biochemistry Analyzer (Yellow Springs Instrument Co., Yellow Springs, Ohio) and insulin concentrations using an ELISA assay.

Illustrative of the invention, the compound of Example 9 demonstrates an $EC_{50}$ of about 3 nM in the PPARα receptor binding assay and an $EC_{50}$ of about 1800 nM in the PPARγ receptor binding assay.

The following Examples are intended to illustrate the invention and are not to be construed as being limitations thereon. Temperatures are given in degrees Centigrade. If not mentioned otherwise, all evaporations are performed under reduced pressure, preferably between about 10 and 100 mmHg. The structure of final products, intermediates and starting materials is confirmed by standard analytical methods, e.g., microanalysis and spectroscopic characteristics, e.g., MS, IR and NMR. Abbreviations used are those conventional in the art.

EXAMPLE 1

(R)-1-{2-[3-(5-Methyl-2-phenyl-oxazol-4-yl-methoxy)-phenyl]-acetyl}-pyrrolidine-2-carboxylic acid

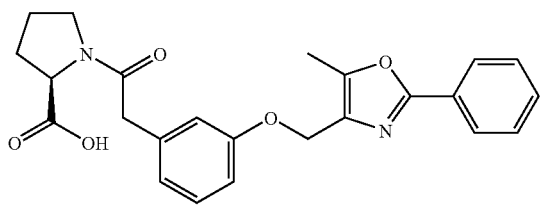

A. (R)-1-[2-(3-Hydroxy-phenyl)-acetyl]-pyrrolidine-2-carboxylic acid ethyl ester To a suspension of 3-hydroxy phenylacetic acid (1.52 g, 10.0 mmol) in 10 mL of DCM is added L-proline methyl ester hydrochloride (1.80 g, 10.0 mmol) followed by the addition of TEA (1.67 mL, 12 mmol), 1-hydroxybenzotriazole (HOBt, 1.17 g, 10 mmol), and EDCl (1.92 g, 10 mmol). The mixture is stirred at RT for 4 days. Ethyl acetate and water is added, and the organic layer is separated and washed with brine, dried over anhydrous sodium sulfate, and concentrated. The crude mixture is purified by flash chromatography (silica gel) eluting with hexane:ethyl acetate (1:2) to give (R)-1-[2-(3-hydroxy-phenyl)-acetyl]-pyrrolidine-2-carboxylic acid ethyl ester as an oil.

B. (R)-1-{2-[3-(5-Methyl-2-phenyl-oxazol-4-ylmethoxy)-phenyl]-acetyl}-pyrrolidine-2-carboxylic acid ethyl ester To a solution of the title A compound, (R)-1-[2-(3-hydroxy-phenyl)-acetyl]-pyrrolidine-2-carboxylic acid ethyl ester (1.0 g, 3.61 mmol) in 10 mL DMF is added potassium carbonate (0.60 g, 4.33 mmol) followed by 4-chloromethyl-5-methyl-2-phenyl-oxazole (0.75 g, 3.61 mmol). The mixture is stirred for 24 h at RT, and partitioned between ethyl acetate and water. The organic layer is separated and washed with brine, dried over anhydrous sodium sulfate, concentrated and purified by flash chromatography (silica gel) eluting with hexane:ethyl acetate (3:7) to give (R)-1-{2-[3-(5-methyl-2-phenyl-oxazol-4-ylmethoxy)-phenyl]-acetyl}-pyrrolidine-2-carboxylic acid ethyl ester.

C. (R)-1-{2-[3-(5-Methyl-2-phenyl-oxazol-4-ylmethoxy)-phenyl]-acetyl}-pyrrolidine-2-carboxylic acid To a solution of the title B compound, (R)-1-{2-[3-(5-methyl-2-phenyl-oxazol-4-ylmethoxy)-phenyl]-acetyl}-pyrrolidine-2-carboxylic acid ethyl ester (1.3 g, 2.9 mmol) in 25 mL of methanol at RT is added 1 N aqueous sodium hydroxide (8.7 mL). The mixture is stirred for 20 h and washed with ethyl acetate. The aqueous layer is acidified with 1 N aqueous hydrochloric acid (HCl), extracted with ethyl acetate, washed with brine, dried over anhydrous sodium sulfate and concentrated to give an oil. The crude product is purified by flash chromatography (silica gel) eluting with ethyl acetate→ethyl acetate:acetic acid (2:1) to give (R)-1-{2-[3-(5-methyl-2-phenyl-oxazol-4-ylmethoxy)-phenyl]-acetyl}-pyrrolidine-2-carboxylic acid as a foam: MS m/z 419.1 [M−1]⁻.

EXAMPLE 2

(R)-1-[3-(5-Methyl-2-phenyl-oxazol-4-ylmethoxy)-phenylsulfanylcarbonyl]-pyrrolidine-2-carboxylic acid

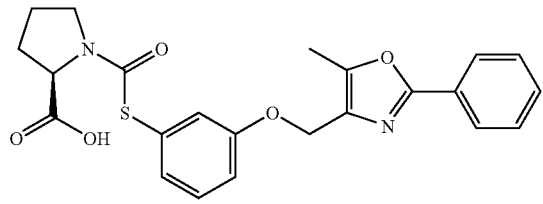

A. (R)-1-Chlorocarbonyl-pyrrolidine-2-carboxylic acid ethyl ester

To a stirred solution of (R)-pyrrolidine-2-carboxylic acid ethyl ester hydrochloride (4.0 g, 22.3 mmol) and TEA (9.02 g, 89.2 mmol) in DCM (40 mL) is added triphosgene (8.0 g, 26.8 mmol) at 0° C. The reaction mixture is allowed to warm gradually to RT and stirred for 3 h.

The reaction mixture is diluted with DCM, washed with water and brine, dried over anhydrous magnesium sulfate and concentrated at reduced pressure. The crude product is purified on a Biotage 40M column using 20% ethyl acetate in hexane to yield (R)-1-chlorocarbonyl-pyrrolidine-2-carboxylic acid ethyl ester as a clear oil.

B. (R)-1-[3-(t-Butyl-dimethyl-silanyloxy)-phenylsulfanylcarbonyl]-pyrrolidine-2-carboxylic acid ethyl ester To a stirred suspension of sodium hydride (0.25 g, 6.3 mmol) in anhydrous THF (20 mL) is added 3-(t-butyl-dimethyl-silanyloxy)-benzenethiol (1.3 g, 5.22 mmol) at RT. After 10 min, the title A compound, (R)-1-chlorocarbonyl-pyrrolidine-2-carboxylic acid ethyl ester (1.1 g, 5.22 mmol) is added and the reaction is stirred for 24 h. The reaction mixture is diluted with ethyl acetate, washed with water and brine, dried over anhydrous magnesium sulfate and concentrated at reduced pressure. The crude product is purified on a Biotage 40M column using 25% ethyl acetate in hexane to yield (R)-1-[3-(t-butyl-dimethyl-silanyloxy)-phenyl-sulfanylcarbonyl]-pyrrolidine-2-carboxylic acid ethyl ester as a clear oil.

C. (R)-1-(3-Hydroxy-phenylsulfanylcarbonyl)-pyrrolidine-2-carboxylic acid ethyl ester To the title B compound, (R)-1-[3-(t-butyl-dimethyl-silanyloxy)-phenylsulfanyl-carbonyl]-pyrrolidine-2-carboxylic acid ethyl ester (1.5 g, 3.66 mmol) in a flask at RT, is added 1 M solution of n-tetrabutylammonium fluoride (14.6 mL, 14.6 mmol) in THF and the reaction is stirred for 4 h. The reaction mixture is concentrated at reduced pressure, diluted with ethyl acetate, washed with water and brine, dried over anhydrous magnesium sulfate and concentrated. The crude (R)-1-(3-hydroxy-phenylsulfanylcarbonyl)-pyrrolidine-2-carboxylic acid ethyl ester is used in the next step without further purification.

D. (R)-1-[3-(5-Methyl-2-phenyl-oxazol-4-ylmethoxy)-phenylsulfanylcarbonyl]-pyrrolidine-2-carboxylic acid ethyl ester To a stirred solution of the title C compound, 1-(3-hydroxy-phenylsulfanylcarbonyl)-pyrrolidine-2-carboxylic acid ethyl ester (1.1 g, 3.73 mmol) and potassium carbonate (0.78 g, 5.59 mmol) in DMF (25 mL) is added 4-chloromethyl-5-methyl-2-phenyl-oxazole (0.78 g, 3.73 mmol) at RT. The reaction mixture is stirred for 16 h. The stirring is continued for another 3 h at 40° C. The reaction mixture is cooled to RT, diluted with ethyl acetate, washed with water and brine, dried over anhydrous magnesium sulfate and concentrated at reduced pressure. The crude product is purified on a Biotage 40M column using 25% ethyl acetate in hexane to yield (R)-1-[3-(5-methyl-2-phenyl-oxazol-4-ylmethoxy)-phenyl-sulfanylcarbonyl]-pyrrolidine-2-carboxylic acid ethyl ester as a clear, heavy oil.

E. (R)-1-[3-(5-Methyl-2-phenyl-oxazol-4-ylmethoxy)-phenylsulfanylcarbonyl]-pyrrolidine-2-carboxylic acid To a stirred solution of the title D compound, (R)-1-[3-(5-methyl-2-phenyl-oxazol-4-ylmethoxy)-phenylsulfanylcarbonyl]-pyrrolidine-2-carboxylic acid ethyl ester (1.5 g, 3.22 mmol) in methanol (15 mL) is added sodium hydroxide (0.26 g, 6.44 mmol) in water (10 mL) at RT. The reaction mixture is stirred for 4 h. The reaction mixture is concentrated at reduced pressure, poured into water, the aqueous layer is separated, washed with ethyl acetate twice, acidified with concentrated HCl and extracted three times with ethyl acetate. The combined ethyl acetate extract is concentrated and triturated with 1:1 methyl-t-butyl ether and hexane to give (R)-1-[3-(5-methyl-2-phenyl-oxazol-4-ylmethoxy)-phenylsulfanylcarbonyl]-pyrrolidine-2-carboxylic acid as a white solid.

EXAMPLE 3

(R)-Pyrrolidine-1,2-dicarboxylic acid-1-[3-(5-methyl-2-phenyl-oxazol-4-ylmethoxy)-phenyl]ester

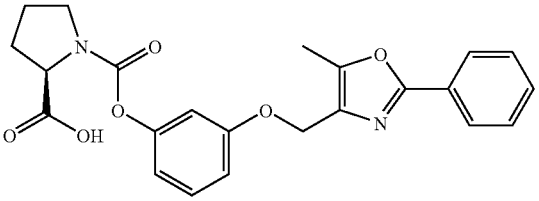

. Acetic acid 3-(5-methyl-2-phenyl-oxazol-4-ylmethoxy)-phenyl ester

To a stirred solution of acetic acid 3-hydroxyphenyl ester (5.0 g, 32.86 mmol) and potassium carbonate (6.8 g, 49.3 mmol) in DMF (40 mL) is added 4-chloromethyl-5-methyl- 2-phenyl-oxazole (6.8 g, 32.86 mmol) at RT. The reaction mixture is stirred for 3 h at RT followed by 24 h at 70° C. The reaction mixture is cooled to RT, diluted with ethyl acetate, washed with water and brine, dried over anhydrous magnesium sulfate and concentrated at reduced pressure. The crude product is purified on a Biotage 40M column using 20% ethyl acetate in hexane to yield acetic acid-3-(5-methyl-2-phenyl-oxazol-4-ylmethoxy)-phenyl ester as a clear oil.

B. 3-(5-Methyl-2-phenyl-oxazol-4-ylmethoxy)-phenol

To a stirred solution of the title A compound, acetic acid 3-(5-methyl-2-phenyl-oxazol-4-ylmethoxy)-phenyl ester (3.92 g, 12.14 mmol) in methanol (15 mL) is added sodium hydroxide (0.97 g, 24.27 mmol) in water (15 mL) at RT. The reaction mixture is stirred for 4 h. The reaction mixture is concentrated at reduced pressure, poured into water, the aqueous layer is separated, washed with ethyl acetate twice, acidified with concentrated HCl and extracted three times with ethyl acetate. The combined ethyl acetate extract is dried over anhydrous magnesium sulfate and concentrated under reduced pressure to give 3-(5-methyl-2-phenyl-oxazol-4-ylmethoxy)-phenol as a white solid.

C. (R)-Pyrrolidine-1,2-dicarboxylic acid-2-ethyl ester-1-[3-(5-methyl-2-phenyl-oxazol-4-ylmethoxy)-phenyl]ester To a stirred suspension of sodium hydride (0.24 g, 5.83 mmol) in anhydrous THF (25 mL) is added the title B compound, 3-(5-methyl-2-phenyl-oxazol-4-ylmethoxy)phenol (1.4 g, 4.87 mmol) at RT. After 10 min, the title A compound of Example 2, (R)-1-chlorocarbonyl-pyrrolidine-2-carboxylic acid ethyl ester (1.0 g, 4.87 mmol) is added and the reaction is stirred for 5 h. The reaction mixture is diluted with ethyl acetate, washed with water and brine, dried over anhydrous magnesium sulfate and concentrated at reduced pressure. The crude product is purified on a Biotage 40M column using 25% ethyl acetate in hexane to yield (R)-pyrrolidine-1,2-dicarboxylic acid-2-ethyl ester-1-[3-(5-methyl-2-phenyl-oxazol-4-ylmethoxy)-phenyl]ester as a clear oil.

D. (R)-Pyrrolidine-1,2-dicarboxylic acid 1-[3-(5-methyl-2-phenyl-oxazol-4-ylmethoxy)-phenyl]ester To a stirred solution of the title C compound, (R)-pyrrolidine-1,2-dicarboxylic acid-2-ethyl ester-1-[3-(5-methyl-2-phenyl-oxazol-4-ylmethoxy)-phenyl]ester (1.4 g, 3.11 mmol) in methanol (20 mL) is added sodium hydroxide (0.25 g, 6.22 mmol) in water (5 mL) at RT. The reaction mixture is stirred for 4 h. The reaction mixture is concentrated at reduced pressure, poured into water, the aqueous layer is separated, washed with ethyl acetate twice, acidified with concentrated HCl and extracted three times with ethyl acetate. The combined ethyl acetate extract is concentrated and triturated with 1:1 methyl-t-butyl ether to hexane to give (R)-pyrrolidine-1,2-dicarboxylic acid 1-[3-(5-methyl-2-phenyl-oxazol-4-ylmethoxy)-phenyl]ester as a white solid.

EXAMPLE 4

(R)-1-{2-Methyl-2-[3-(5-methyl-2-phenyl-oxazol-4-ylmethoxy)-phenyl]-propionyl}-pyrrolidine-2-carboxylic acid

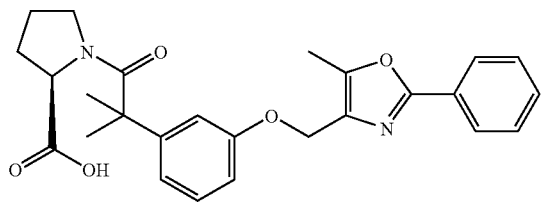

A. [3-(5-Methyl-2-phenyl-oxazol-4-ylmethoxy)-phenyl]-acetic acid methyl ester

To a stirred solution of (3-hydroxy-phenyl)-acetic acid methyl ester (4.26 g, 25.66 mmol) and potassium carbonate (7.1 g, 51.33 mmol) in DMF (60 mL) is added 4-chloromethyl-5-methyl-2-phenyl-oxazole (5.33 g, 25.66 mmol) at RT. The reaction mixture is stirred for 16 h at 40° C. followed by 16 h at 60° C. The reaction mixture is cooled to RT, diluted with ethyl acetate, washed with water and brine, dried over anhydrous magnesium sulfate and concentrated at reduced pressure. The crude product is purified on a Biotage 40M column using 25% ethyl acetate in hexane to yield [3-(5-methyl-2-phenyl-oxazol-4-ylmethoxy)-phenyl]-acetic acid methyl ester as a white solid.

B. 2-Methyl-2-[3-(5-methyl-2-phenyl-oxazol-4-ylmethoxy)-phenyl]-propionic acid methyl ester To a stirred suspension of sodium hydride (2.2 g, 54.75 mmol) in anhydrous tetrahydrofuran (40 mL) is added dropwise a solution of the title A compound, [3-(5-methyl-2-phenyl-oxazol-4-ylmethoxy)-phenyl]-acetic acid methyl ester (6.15 g, 18.25 mmol) in THF (20 mL) at RT. After 1 h, iodomethane (6.0 g, 41.97 mmol) is added dropwise and the reaction is stirred for 16 h. The reaction mixture is then diluted with ethyl acetate, washed with water and brine, dried over anhydrous magnesium sulfate and concentrated at reduced pressure. The crude product is purified on a Biotage 40M column using 15% ethyl acetate in hexane to yield 2-methyl-2-[3-(5-methyl-2-phenyl-oxazol-4-ylmethoxy)-phenyl]-propionic acid methyl ester as a clear oil.

C. 2-Methyl-2-[3-(5-methyl-2-phenyl-oxazol-4-ylmethoxy)-phenyl]-propionic acid

To a stirred solution of the title B compound, 2-methyl-2-[3-(5-methyl-2-phenyl-oxazol-4-ylmethoxy)-phenyl]-propionic acid methyl ester (3.45 g, 9.45 mmol) in methanol (30 mL) is added sodium hydroxide (1.51 g, 37.81 mmol) in water (10 mL) at RT. The reaction mixture is stirred at 70° C. for 4 h. The reaction mixture is concentrated, poured into water, the aqueous layer is separated, washed with ethyl acetate twice, acidified with concentrated HCl and extracted three times with ethyl acetate. The combined ethyl acetate extract is dried over magnesium sulfate and concentrated to give 2-methyl-2-[3-(5-methyl-2-phenyl-oxazol-4-ylmethoxy)-phenyl]-propionic acid as a white solid.

D. (R)-1-{2-Methyl-2-[3-(5-methyl-2-phenyl-oxazol-4-ylmethoxy)-phenyl]-propionyl}-pyrrolidine-2-carboxylic acid ethyl ester To a stirred solution of (R)-pyrrolidine-2-carboxylic acid ethyl ester hydrochloride (1.7 g, 9.4 mmot), TEA (1.0 g, 10.3 mmol) and the title C compound, 2-methyl-2-[3-(5-methyl-2-phenyl-oxazol-4-ylmethoxy)-phenyl]-propionic acid (3.0 g, 8.55 mmol) in DCM (50 mL) is added EDCl (2.0 g, 10.3 mmol) and 1-hydroxy-7-azabenzotriazole (HOAt, 1.2 g, 8.55 mmol) at RT. The reaction mixture is stirred for 48 h. The reaction mixture is diluted with ethyl acetate, washed with 2 N aqueous HCl, water, 2 N aqueous sodium hydroxide, water and brine, dried over anhydrous magnesium sulfate and concentrated at reduced pressure. The crude product is purified on a Biotage 40M column using 35% ethyl acetate in hexane to yield (R)-1-{2-methyl-2-[3-(5-methyl-2-phenyl-oxazol-4-ylmethoxy)-phenyl]-propionyl}-pyrrolidine-2-carboxylic acid ethyl ester as a clear oil.

E. (R)-1-{2-Methyl-2-[3-(5-methyl-2-phenyl-oxazol-4-ylmethoxy)-phenyl]-propionyl}-pyrrolidine-2-carboxylic acid To a stirred solution of title D compound, (R)-{2-methyl-2-[3-(5-methyl-2-phenyl-oxazol-4-ylmethoxy)-phenyl]-propionyl}-pyrrolidine-2-carboxylic acid ethyl ester (0.47 g, 0.99 mmol) in methanol (25 mL) is added sodium hydroxide (0.16 g, 3.95 mmol) in water (5 mL) at RT. The reaction mixture is stirred for 16 h. The reaction mixture is concentrated at reduced pressure, poured into water, the aqueous layer is separated, washed with ethyl acetate twice, acidified with concentrated HCl and extracted three times with ethyl acetate. The combined ethyl acetate extract is dried and concentrated to give (R)-1-{2-methyl-2-[3-(5-methyl-2-phenyl-oxazol-4-ylmethoxy)-phenyl]-propionyl}-pyrrolidine-2-carboxylic acid as a white solid: MS m/z 447.3 [M−1]⁻.

The following compounds are prepared as illustrated herein above.

| Example | Structure | Chemical name | MS, m/z |
|---|---|---|---|
| 5 | 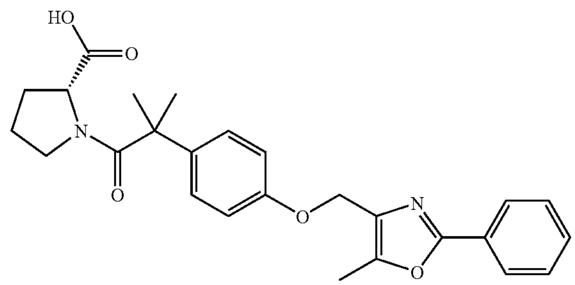 | (R)-1-{2-[4-(5-Methyl-2-phenyl-oxazol-4-ylmethoxy)-phenyl]-acetyl}-pyrrolidine-2-carboxylic acid | [M−1]⁻ 447.2 |
| 6 | 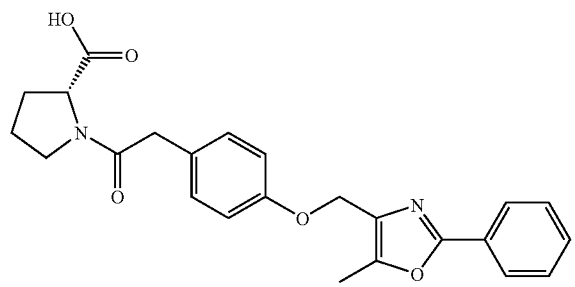 | (R)-1-{2-[4-(5-Methyl-2-phenyl-oxazol-4-ylmethoxy)-phenyl]-acetyl}-pyrrolidine-2-carboxylic acid | [M−1]⁻ 419.1 |
| 7 | 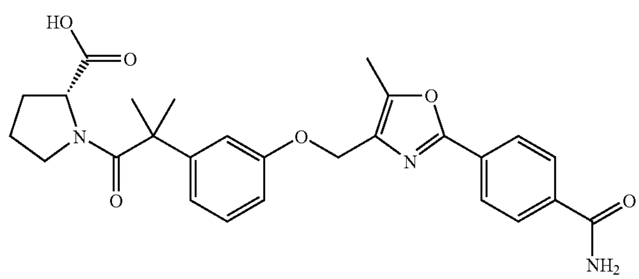 | (R)-1-(2-{3-[2-(4-Carbamoylphenyl)-5-methyl-oxazol-4-ylmethoxy]-phenyl}-2-methyl-propionyl)-pyrrolidine-2-carboxylic acid | [M−1]⁻ 490.1 |
| 8 | 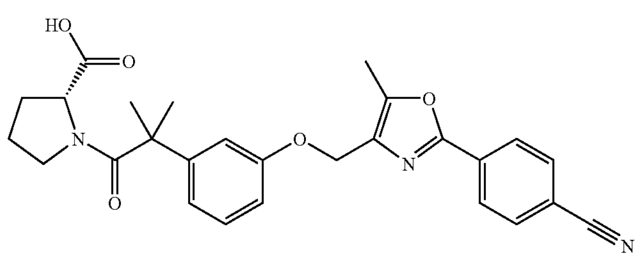 | (R)-1-(2-{3-[2-(4-Cyano-phenyl)-5-methyl-oxazol-4-ylmethoxy]phenyl}-2-methyl-propionyl)-pyrrolidine-2-carboxylic acid | [M−1]⁻ 472.1 |
| 9 | 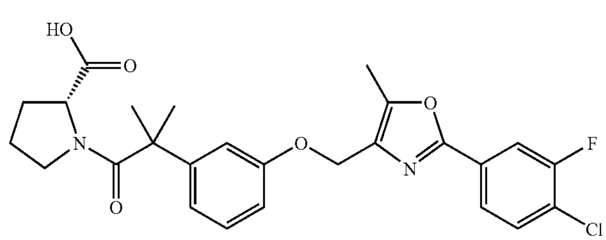 | (R)-1-(2-{3-[2-(4-Chloro-3-fluoro-phenyl)-5-methyl-oxazol-4-yl-methoxy]-phenyl}-2-methyl-propionyl)-pyrrolidine-2-carboxylic acid | [M−1]⁻ 499.0 |

-continued

| Example | Structure | Chemical name | MS, m/z |
|---|---|---|---|
| 10 | 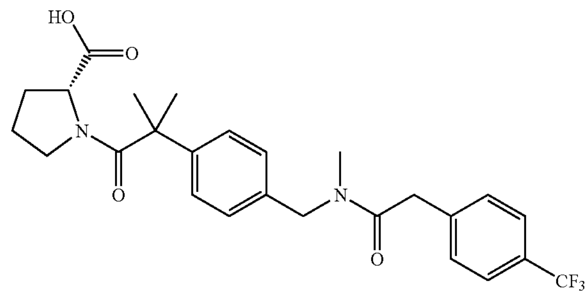 | (R)-1-{2-Methyl-2-[4-({methyl-[2-(4-trifluoromethyl-phenyl)-acetyl]-amino}-methyl)-phenyl]-propionyl}-pyrrolidine-2-carboxylic acid | [M−1]⁻ 489.2 |
| 11 | 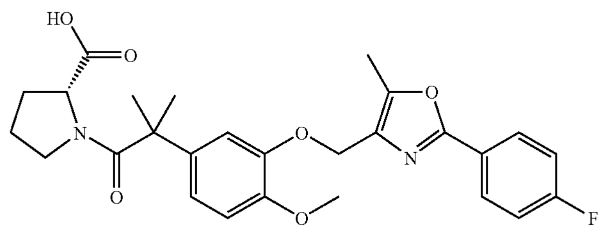 | (R)-1-(2-{3-[2-(4-Fluoro-phenyl)-5-methyl-oxazol-4-ylmethoxy]-4-methoxy-phenyl}-2-methyl-propionyl)-pyrrolidine-2-carboxylic acid | [M−1]⁻ 495.3 |
| 12 | 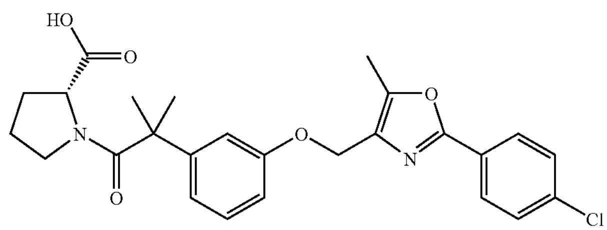 | (R)-1-(2-{3-[2-(4-Chloro-phenyl)-5-methyl-oxazol-4-ylmethoxy]-phenyl}-2-methyl-propionyl)-pyrrolidine-2-carboxylic acid | [M−1]⁻ 481.2 |
| 13 | 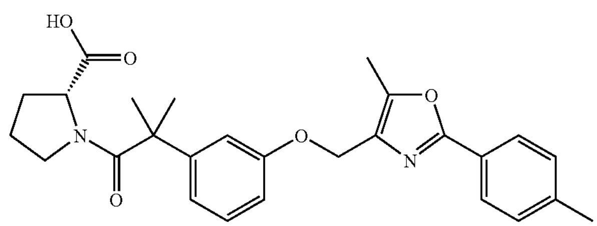 | (R)-1-{2-Methyl-2-[3-(5-methyl-2-p-tolyl-oxazol-4-ylmethoxy)-phenyl]-propionyl}-pyrrolidine-2-carboxylic acid | [M−1]⁻ 461.3 |
| 14 | 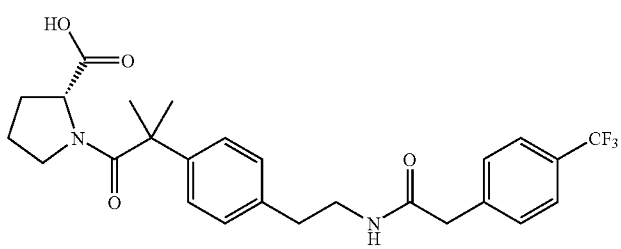 | (R)-1-[2-(4-{2-[2-(4-Trifluoromethyl-phenyl)-acetylamino]-ethyl}-phenyl)-acetyl]-pyrrolidine-2-carboxylic acid | [M−1]⁻ 461.2 |
| 15 | 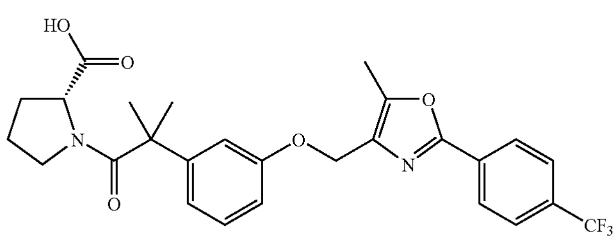 | (R)-1-(2-Methyl-2-{3-[5-methyl-2-(4-trifluoromethyl-phenyl)-oxazol-4-ylmethoxy]-phenyl}-propionyl)-pyrrolidine-2-carboxylic acid | [M−1]⁻ 515.3 |

| Example | Structure | Chemical name | MS, m/z |
|---|---|---|---|
| 16 | 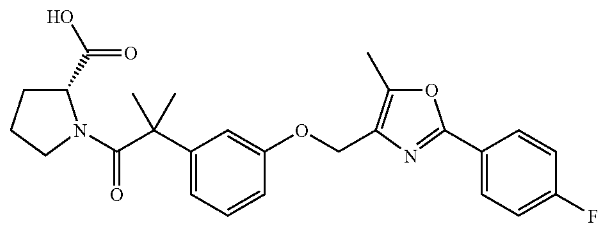 | (R)-1-(2-{3-[2-(4-Fluoro-phenyl)-5-methyl-oxazol-4-ylmethoxy]-phenyl}-2-methyl-propionyl)-pyrrolidine-2-carboxylic acid | [M−1]⁻ 467.3 |
| 17 | 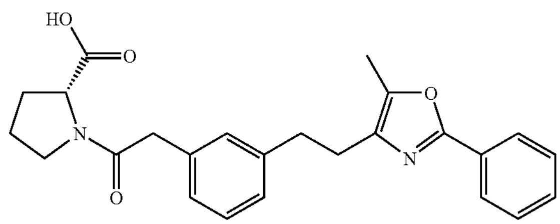 | (R)-1-(2-{3-[2-(5-Methyl-2-phenyl-oxazol-4-yl)-ethyl]-phenyl}-acetyl)-pyrrolidine-2-carboxylic acid | [M−1]⁻ 417.2 |
| 18 | 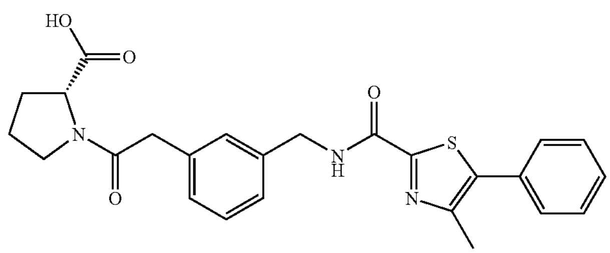 | (R)-1-[2-(3-{[(4-Methyl-5-phenyl-thiazole-2-carbonyl)-amino]-methyl}-phenyl)-acetyl]-pyrrolidine-2-carboxylic acid | [M−1]⁻ 462.2 |
| 19 | 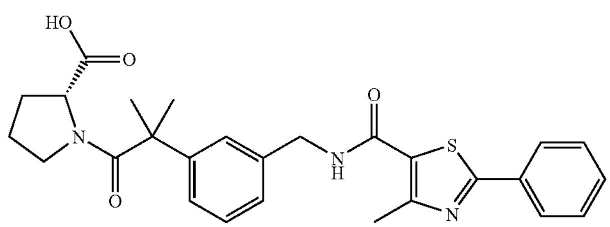 | (R)-1-[2-Methyl-2-(3-{[(4-methyl-2-phenyl-thiazole-5-carbonyl)-amino]-methyl}-phenyl)-propionyl]-pyrrolidine-2-carboxylic acid | [M−1]⁻ 490.2 |
| 20 | 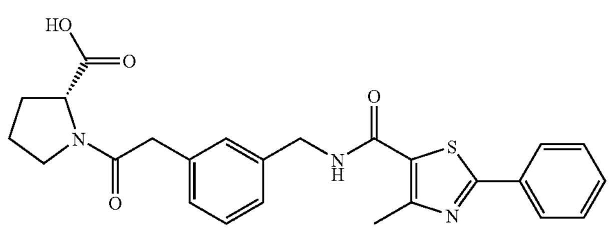 | (R)-1-[2-(3-{[(4-Methyl-2-phenyl-thiazole-5-carbonyl)-amino]-methyl}-phenyl)-acetyl]-pyrrolidine-2-carboxylic acid | [M−1]⁻ 462.1 |
| 21 | 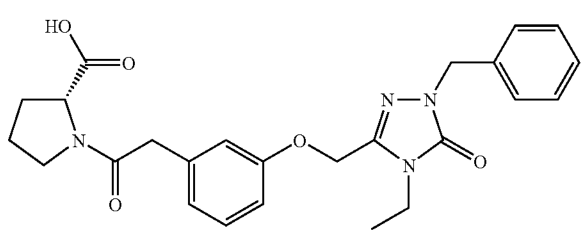 | (R)-1-{2-[3-(1-Benzyl-4-ethyl-5-oxo-4,5-dihydro-1H-[1,2,4]triazol-3-ylmethoxy)-phenyl]-acetyl}-pyrrolidine-2-carboxylic acid | [M−1]⁻ 463.2 |

-continued

| Example | Structure | Chemical name | MS, m/z |
|---|---|---|---|
| 22 | 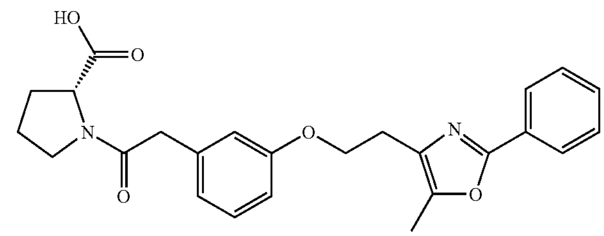 | (R)-1-(2-{3-[2-(5-Methyl-2-phenyl-oxazol-4-yl)-ethoxy]-phenyl}-acetyl)-pyrrolidine-2-carboxylic acid | [M−1]⁻ 433.2 |
| 23 | 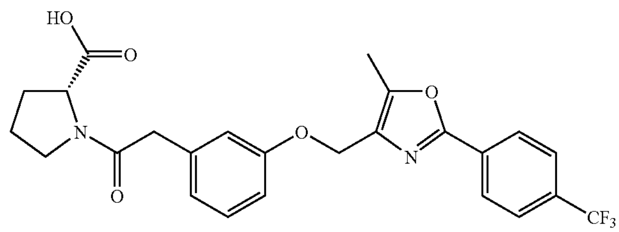 | (R)-1-(2-{3-[5-Methyl-2-(4-trifluoromethyl-phenyl)-oxazol-4-ylmethoxy]-phenyl}-acetyl)-pyrrolidine-2-carboxylic acid | [M−1]⁻ 487.1 |
| 24 | 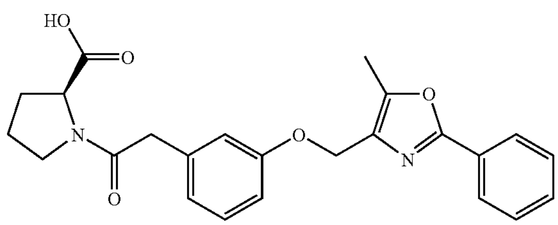 | (S)-1-{2-[3-(5-Methyl-2-phenyl-oxazol-4-ylmethoxy)-phenyl]-acetyl}-pyrrolidine-2-carboxylic acid | [M−1]⁻ 419.2 |
| 25 | 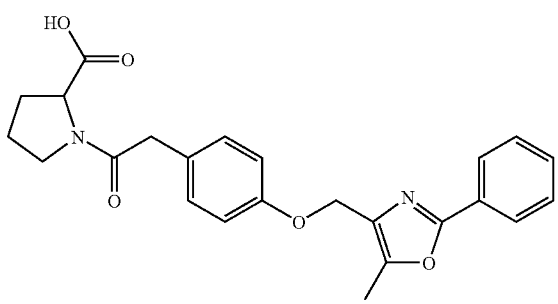 | 1-{2-[3-(5-Methyl-2-phenyl-oxazol-4-ylmethoxy)-phenyl]-acetyl}-pyrrolidine-2-carboxylic acid | [M−1]⁻ 419.2 |
| 26 | 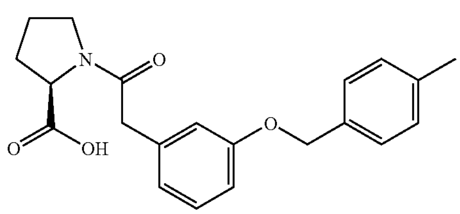 | (R)-1-{2-[3-(4-Methyl-benzyloxy)-phenyl]-acetyl}-pyrrolidine-2-carboxylic acid | [M−1]⁻ 352.2 |
| 27 | 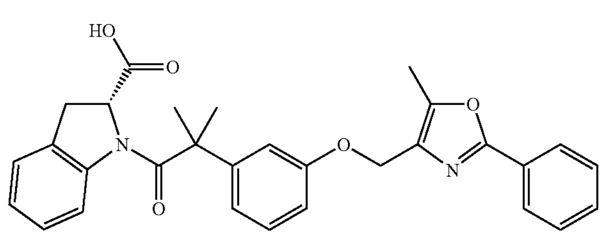 | (R)-1-{2-Methyl-2-[3-(5-methyl-2-phenyl-oxazol-4-ylmethoxy)-phenyl]-propionyl}-2,3-dihydro-1H-indole-2-carboxylic acid | [M−1]⁻ 495.1 |

-continued

| Example | Structure | Chemical name | MS, m/z |
|---|---|---|---|
| 28 | 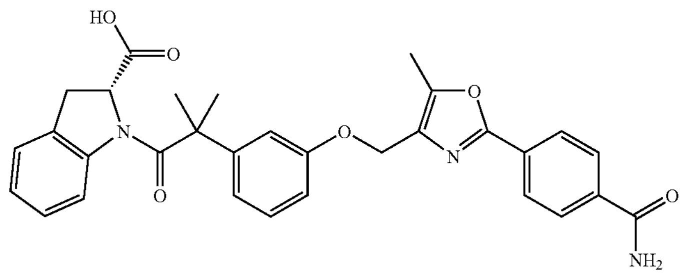 | (R)-1-(2-{3-[2-(4-Carbamoyl-phenyl)-5-methyl-oxazol-4-ylmethoxy]-phenyl}-2-methyl-propionyl)-2,3-dihydro-1H-indole-2-carboxylic acid | [M−1]⁻ 538.1 |
| 29 | 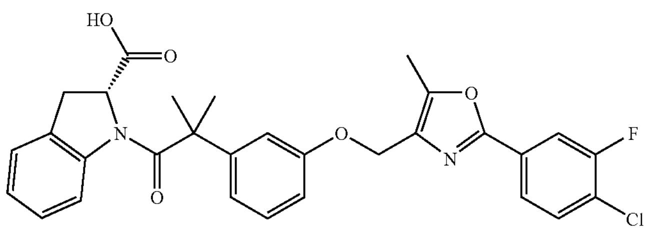 | (R)-1-(2-{3-[2-(4-Chloro-3-fluoro-phenyl)-5-methyl-oxazol-4-ylmethoxy]-phenyl}-2-methyl-propionyl)-2,3-dihydro-1H-indole-2-carboxylic acid | [M−1]⁻ 547.2 |
| 30 | 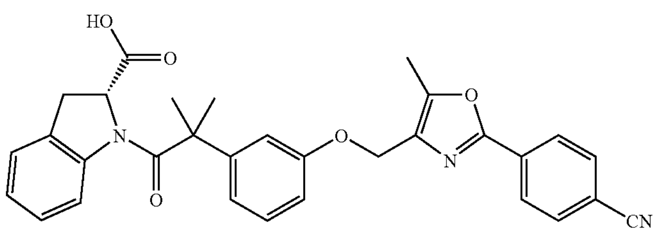 | (R)-1-(2-{3-[2-(4-Cyano-phenyl)-5-methyl-oxazol-4-ylmethoxy]-phenyl}-2-methyl-propionyl)-2,3-dihydro-1H-indole-2-carboxylic acid | [M−1]⁻ 520.2 |
| 31 | 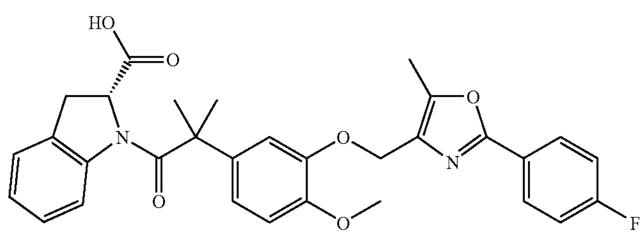 | (R)-1-(2-{3-[2-(4-Fluoro-phenyl)-5-methyl-oxazol-4-ylmethoxy]-4-methoxy-phenyl}-2-methyl-propionyl)-2,3-dihydro-1H-indole-2-carboxylic acid | [M−1]⁻ 543.4 |
| 32 | 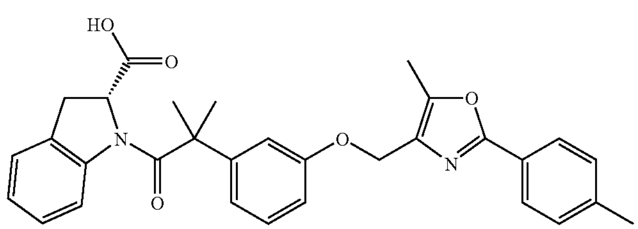 | (R)-1-{2-Methyl-2-[3-(5-methyl-2-p-tolyl-oxazol-4-ylmethoxy)-phenyl]-propionyl}-2,3-dihydro-1H-indole-2-carboxylic acid | [M−1]⁻ 509.4 |
| 33 | 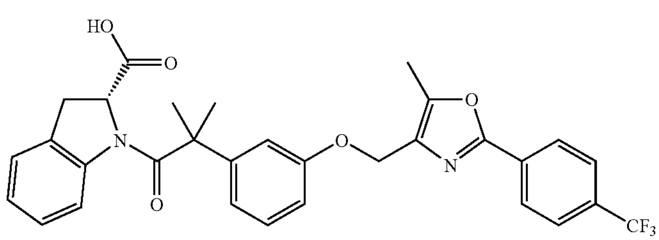 | (R)-1-(2-Methyl-2-{3-[5-methyl-2-(4-trifluoromethyl-phenyl)-oxazol-4-ylmethoxy]-phenyl}-propionyl)-2,3-dihydro-1H-indole-2-carboxylic acid | [M−1]⁻ 563.4 |

| Example | Structure | Chemical name | MS, m/z |
|---|---|---|---|
| 34 | 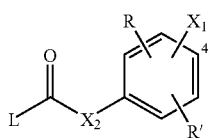 | (R)-1-(2-{3-[2-(4-Chloro-phenyl)-5-methyl-oxazol-4-ylmethoxy]-pheny}-2-methyl-propionyl)-2,3-dihydro-1H-indole-2-carboxylic acid | [M−1]⁻ 529.3 |
| 35 | 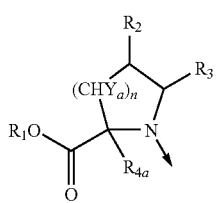 | (R)-1-(2-{3-[2-(4-Fluoro-phenyl)-5-methyl-oxazol-4-ylmethoxy]-phenyl}-2-methyl-propionyl)-2,3-dihydro-1H-indole-2-carboxylic acid | [M−1]⁻ 513.3 |

What is claimed is:

1. A compound of the formula (I)

wherein L is a radical of the formula:

(II)

in which
R$_1$ is hydrogen, optionally substituted alkyl, aryl, heteroaryl, aralkyl or cycloalkyl;
R$_2$ is hydrogen, hydroxy, oxo, optionally substituted alkyl, aryl, aralkyl, alkoxy, aryloxy, aralkoxy, alkylthio, arylthio or aralkylthio;
R$_3$ is hydrogen; or
R$_2$ and R$_3$ combined are alkylene which together with the carbon atoms to which they are attached form a fused 5- to 7-membered ring; or
R$_2$ and R$_3$ combined are a bond between the carbon atoms to which they are attached;
n is zero or an integer of 1 or 2;
Y$_a$ is hydrogen; or
Y$_a$ and R$_2$ combined are a bond between the carbon atoms to which they are attached;
R$_{4a}$ is hydrogen; or
R$_{4a}$ and Y$_a$ combined are a bond between the carbon atoms to which they are attached;

R and R' are independently hydrogen, halogen, optionally substituted alkyl, alkoxy, aralkyl or heteroaralkyl; or
R and R' combined together with the carbon atoms to which they are attached form an optionally substituted fused 5- to 6-membered aromatic or heteroaromatic ring provided that R and R' are attached to carbon atoms adjacent to each other; or
R—C and R'—C may independently be replaced by nitrogen;
X$_1$ is -Z-(CH$_2$)$_p$-Q-W wherein
Z is a bond, O, S, S(O) or S(O)$_2$; or
Z is —C(O)NR$_5$— in which
R$_5$ is hydrogen, alkyl or aralkyl;
p is an integer from 1 to 8;
Q is a bond; or
Q is —O(CH$_2$)$_r$— or —S(CH$_2$)$_r$— in which r is zero or an integer from 1 to 8; or
Q is —O(CH$_2$)$_{1-8}$O—, —S(CH$_2$)$_{1-8}$O—, —S(CH$_2$)$_{1-8}$S— or —C(O)—; or
Q is —C(O)NR$_6$— in which
R$_6$ is hydrogen, optionally substituted alkyl, cycloalkyl, aryl, heteroaryl, aralkyl or heteroaralkyl; or
Q is —NR$_7$—, —NR$_7$C(O)—, —NR$_7$C(O)NR$_8$— or —NR$_7$C(O)O— in which
R$_7$ is hydrogen, optionally substituted alkyl, cycloalkyl, aryl, heteroaryl, aralkyl or heteroaralkyl;
R$_8$ is hydrogen, alkyl or aralkyl;
W is oxazole;
X$_2$ is —C(R$_9$)$_2$—, O, S or —NR$_{10}$— in which
R$_9$ is hydrogen or lower alkyl;
R$_{10}$ is hydrogen, alkyl or aralkyl;
or an optical isomer thereof; or a mixture of optical isomers thereof; or a pharmaceutically acceptable salt thereof.

2. The compound according to claim 1 of the formula

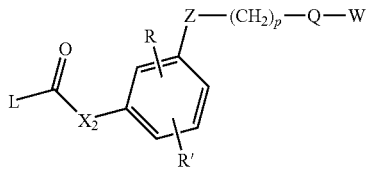
(IA)

wherein L is a radical of the formula:

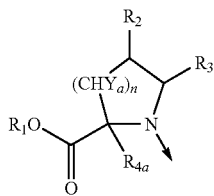
(II)

in which
R$_1$ is hydrogen, optionally substituted alkyl, aryl, heteroaryl, aralkyl or cycloalkyl;
R$_2$ is hydrogen, hydroxy, oxo, optionally substituted alkyl, aryl, aralkyl, alkoxy, aryloxy, aralkoxy, alkylthio, arylthio or aralkylthio;
R$_3$ is hydrogen; or
R$_2$ and R$_3$ combined are alkylene which together with the carbon atoms to which they are attached form a fused 5- to 7-membered ring; or
R$_2$ and R$_3$ combined are a bond between the carbon atoms to which they are attached;
n is 1;
Y$_a$ is hydrogen; or
Y$_a$ and R$_2$ combined are a bond between the carbon atoms to which they are attached;
R$_{4a}$ is hydrogen; or
R$_{4a}$ and Y$_a$ combined are a bond between the carbon atoms to which they are attached;
R and R' are independently hydrogen, halogen, optionally substituted alkyl, alkoxy, aralkyl or heteroaralkyl; or
R and R' combined together with the carbon atoms to which they are attached form an optionally substituted fused 5- to 6-membered aromatic or heteroaromatic ring provided that R and R' are attached to carbon atoms adjacent to each other; or
Z is a bond, O or S;
p is an integer from 1 to 8;
Q is a bond; or
Q is —O(CH$_2$)$_r$— or —S(CH$_2$)$_r$— in which r is zero or an integer from 1 to 8; or
Q is —C(O)NR$_6$— in which
R$_6$ is hydrogen, optionally substituted alkyl, cycloalkyl, aryl, heteroaryl, aralkyl or heteroaralkyl; or
Q is —NR$_7$—, —NR$_7$C(O)—, —NR$_7$C(O)NR$_8$— or —NR$_7$C(O)O— in which
R$_7$ is hydrogen, optionally substituted alkyl, cycloalkyl, aryl, heteroaryl, aralkyl or heteroaralkyl;
R$_8$ is hydrogen, alkyl or aralkyl;
W is oxazole;
X$_2$ is —C(R$_9$)$_2$—, O, S or —NR$_{10}$— in which
R$_9$ is hydrogen or lower alkyl;
R$_{10}$ is hydrogen or lower alkyl;
or an optical isomer thereof; or a mixture of optical isomers thereof; or a pharmaceutically acceptable salt thereof.

3. The compound according to claim 2, wherein
R$_1$ is hydrogen or optionally substituted alkyl;
R$_2$ and R$_3$ are hydrogen;
Y$_a$ is hydrogen;
R$_{4a}$ is hydrogen;
R and R' are independently hydrogen, halogen, optionally substituted C$_{1-6}$ alkyl or C$_{1-6}$ alkoxy;
p is an integer from 1 to 5;
Q is a bond; or
Q is —O(CH$_2$)$_r$— or —S(CH$_2$)$_r$— in which r is zero or 1; or
Q is —C(O)NR$_6$— in which
R$_6$ is hydrogen or lower alkyl; or
Q is —NR$_7$—, —NR$_7$C(O)—, —NR$_7$C(O)NR$_8$— or —NR$_7$C(O)O— in which
R$_7$ is hydrogen or optionally substituted alkyl;
R$_8$ is hydrogen or alkyl;
X$_2$ is —C(R$_9$)$_2$—, O, S or —NR$_{10}$— in which
R$_9$ is hydrogen or methyl;
R$_{10}$ is hydrogen;
or an optical isomer thereof; or a mixture of optical isomers thereof; or a pharmaceutically acceptable salt thereof.

4. The compound according to claim 3, wherein
R and R' are hydrogen;
Q is a bond; or
Q is —O(CH$_2$)$_r$— or —S(CH$_2$)$_r$— in which r is zero; or
Q is —NR$_7$—, —NR$_7$C(O)—, —NR$_7$C(O)NR$_8$— or —NR$_7$C(O)O— in which
R$_7$ is hydrogen or optionally substituted lower alkyl;
or an optical isomer thereof; or a mixture of optical isomers thereof; or a pharmaceutically acceptable salt thereof.

5. The compound according to claim 4, wherein the asymmetric center in radical L is in the (R) configuration; or a pharmaceutically acceptable salt thereof.

6. The compound according to claim 4, wherein X$_2$ is —C(R$_9$)$_2$— in which R$_9$ is methyl; or a pharmaceutically acceptable salt thereof; or an optical isomer thereof; or a mixture of optical isomers thereof.

7. The compound according to claim 4 of the formula

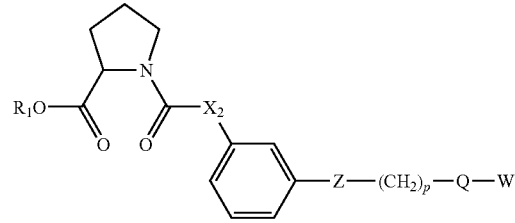
(IB)

wherein
R$_1$ is hydrogen or optionally substituted alkyl;
Z is a bond, O or S;
p is an integer from 1 to 3;
Q is a bond, O or S; or
Q is —NR$_7$C(O)— in which
R$_7$ is hydrogen or optionally substituted lower alkyl;
W is oxazole;
X$_2$ is —C(R$_9$)$_2$, O, S or —NH— in which
R$_9$ is hydrogen or methyl;
or an optical isomer thereof; or a mixture of optical isomers thereof; or a pharmaceutically acceptable salt thereof.

8. The compound according to claim 7, wherein
Z is bond, O or S;
p is an integer of 1 or 2;

Q is a bond;
W is selected from the group consisting of:

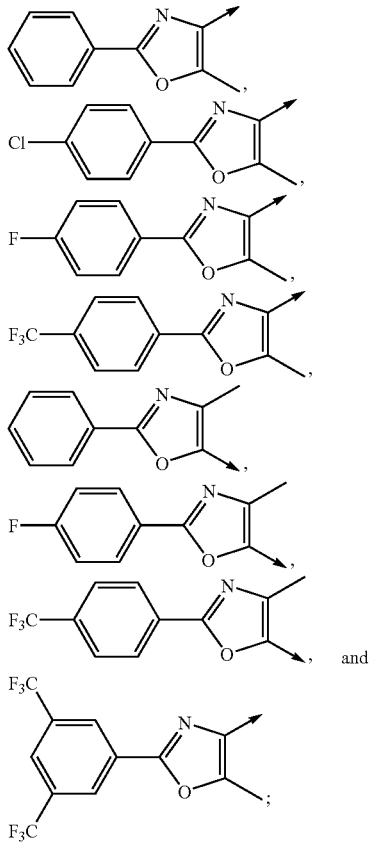

or an optical isomer thereof; or a mixture of optical isomers thereof; or a pharmaceutically acceptable salt thereof.

9. The compound according to claim 8, wherein
Z is O;
p is 1;
$X_2$ is —$C(R_9)_2$— in which $R_9$ is methyl;
W is selected from the group consisting of:

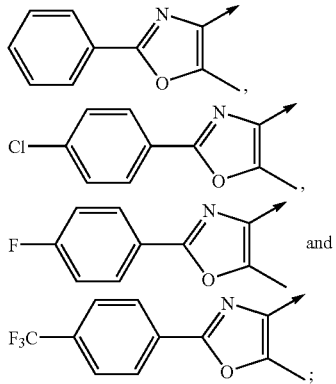

or an optical isomer thereof; or a mixture of optical isomers thereof; or a pharmaceutically acceptable salt thereof.

10. The compound according to claim 9, wherein the asymmetric center in radical L is in the (R) configuration; or a pharmaceutically acceptable salt thereof.

11. The compound according to claim 7, wherein
Z is a bond;
p is 1;

Q is —$NR_7C(O)$— in which
$R_7$ is hydrogen or methyl;
W is selected from the group consisting of:

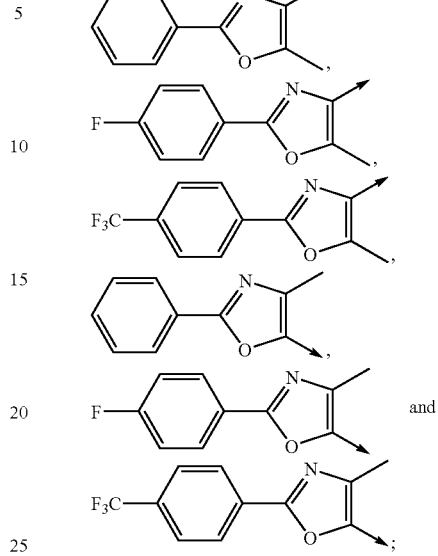

or an optical isomer thereof; or a mixture of optical isomers thereof; or a pharmaceutically acceptable salt thereof.

12. A compound according to claim 1 which is selected from:
(R)-1-{2-[3-(5-Methyl-2-pheny-oxazol-4-ylmethoxy)-phenyl]-acetyl}-pyrrolidine-2-carboxylic acid;
(R)-1-[3-(5Methyl-2-phenyl-oxazol-4-ylmethoxy)-phenylsulfanylcarbonyl]-pyrrolidine-2-carboxylic acid;
(R)-Pyrrolidine-1,2-dicarboxylic acid-1-[3-(5-methyl-2-phenyl-oxazol-4-ylmethoxy)-phenyl]ester;
(R)-1-{2-Methyl-2-[3-(5-methyl-2-phenyl-oxazol-4-ylmethoxy)-phenyl]-propionyl}-pyrrolidine-2-carboxylic acid;
(R)-1-{2-[4-(5-Methyl-2-phenyl-oxazol-4-ylmethoxy)-phenyl]-acetyl}-pyrrolidine-2-carboxylic acid;
(R)-1-{2-[4-(5-Methyl-2-phenyl-oxazol-4-ylmethoxy)-phenyl]-acetyl}-pyrrolidine-2-carboxylic acid;
(R)-1-(2-{3-[2-(4-Carbamoylphenyl)-5-methyl-oxazol-4-ylmethoxy]-phenyl}-2-methyl-propionyl)-pyrrolidine-2-carboxylic acid;
(R)-1-(2-{3-[2-(4-Cyano-phenyl)-5-methyl-oxazol-4-ylmethoxy]phenyl}-2-methyl-propionyl)-pyrrolidine-2-carboxylic acid;
(R)-1-(2-{3-[2-(5-Methyl-2-phenyl-oxazol-4-yl)-ethoxy]-phenyl}-acetyl)-pyrrolidine-2-carboxylic acid;
(R)-1-(2-{3-[5-Methyl-2-(4-trifluoromethyl-phenyl)-oxazol-4-ylmethoxy]-phenyl}-acetyl)-pyrrolidine-2-carboxylic acid;
(S)-1-{2-[3-(5-Methyl-2-phenyl-oxazol-4-ylmethoxy)-phenyl]-acetyl}-pyrrolidine-2-carboxylic acid;
(R)-1-(2-{3-[2-(4-Chloro-3-fluoro-phenylY5-methyl-oxazol-4-yl-methoxy]-phenyl}-2-methyl-propionyl)-pyrrolidine-2-carboxylic acid;
(R)-1-(2-{3-[2-(4-Fluoro-phenyl)-5-methyl-oxazol-4-ylmethoxy]-4-methoxy-phenyl}-2-methyl-propionyly-pyrrolidine-2-carboxylic acid;
(R)-1-(2-{3-[2-(4-Chloro-phenyl)-5-methyl-oxazol-4-ylmethoxy]-phenyl}- 2-methyl-propionyly)-pyrrolidine-2-carboxylic acid;

(R)-1-{2-Methyl-2-3-(5-methyl-2-p-tolyl-oxazol-4-yl-methoxy)-phenyl]-propionyl}-pyrrolidine-2-carboxylic acid;
(R)-1-(2-Methyl-2-{3-[5-methyl-2-(4-trifluoromethyl-phenyl)-oxazol-4-ylmethoxy]-phenyl}-propionyly)-pyrrolidine-2-carboxylic acid;
(R)-1-(2-{3-[2-(4-Fluoro-phenyl)-5-methyl-oxazol-4-yl-methoxy]-phenyl}-2-methyl-propionyl)-pyrrolidine-2-carboxylic acid;
(R)-1-(2-{3-[2-(5-Methyl-2-phenyl-oxazol-4-yl)-ethyl]-phenyl}-acetyl)-pyrrolidine-2-carboxylic acid;
(R)-1-[2-(3-{[(4-Methyl-5-phenyl-thiazole-2-carbonyl)-amino]-methyl}-phenyl)-acetyl]-pyrrolidine-2-carboxylic acid;
(R)-1-[2-Methyl-2-(3-{[(4-methyl-2-phenyl-thiazole-5-carbonyl)-amino]-methyl}-phenyl)-propionyl]-pyrrolidine-2-carboxylic acid;
(R)-1-[2-(3-{[(4-Methyl-2-phenyl-thiazole-5-carbonyl)-amino]-methyl}-phenyl)-acetyl]-pyrrolidine-2-carboxylic acid;
(R)-1-{2-[3-(1-Benzyl-4-ethyl-5-oxo-4,5-dihydro-1H-[1,2,4]triazol-3-ylmethoxy)-phenyl]-acetyl}-pyrrolidine-2-carboxylic acid;
(R)-1-(2-{3-[2-(5-Methyl-2-phenyl-oxazol-4-yl)-ethoxy]-phenyl}-acetyl)-pyrrolidine-2-carboxylic acid;
(R)-1-(2-{3-[5-Methyl-2-(4-trifluoromethyl-phenyl)-oxazol-4-ylmethoxy]-phenyl}-acetyl)-pyrrolidine-2-carboxylic acid;
(S)-1-{2-[3-(5-Methyl-2-phenyl-oxazol-4-ylmethoxy)-phenyl]-acetyl}-pyrrolidine-2-carboxylic acid;
(R)-1-{2-[3-(4-Methyl-benzyloxy)-phenyl]-acetyl}-pyrrolidine-2-carboxylic acid;
(R)-1-{2-Methyl-2-[3-(5-methyl-2-phenyl-oxazol-4-yl-methoxy)-phenyl]-propionyl}2,3-dihydro-1H-indole-2-carboxylic acid;
(R)-1-(2-{3-[2-(4—Carbamoyl-phenylY5-methyl-oxazol-4-ylmethoxy]-phenyl}-2-methyl-propionyl)-2,3-dihydro-1H-indole-2-carboxylic acid;
(R)-1-(2-{3-[2-(4-Chloro-3-fluoro-phenyl 5-methyl-oxazol-4-ylmethoxy]-phenyl}-2-methyl-propionyl)-2,3-dihydro-1H-indole-2-carboxylic acid;
(R)-1-(2-{3-[2-(4—Cyano-phenyl)-5-methyl-oxazol-4-ylmethoxy]-phenyl}-2-methyl-propionyl)-2,3-dihydro-1H-indole-2-carboxylic acid;
(R)-1-(2-{3-[2-(4-Fluoro-phenyl)-5-methyl-oxazol-4-yl-methoxy]-4-methoxy-phenyl}-2-methyl-propionyl)-2,3-dihydro-1H-indole-2-carboxylic acid;
(R)-1-{2-Methyl-2-[3-(5-methyl-2-p-tolyi-oxazol-4-yl-methoxy)-phenyl]-propionyl}-2,3-dihydro-1H-indole-2-carboxylic acid;
(R)-1-(2-Methyl-2-{3-[5-methyl-2-(4-trifluoromethyl-phenyl)-oxazol-4-ylmethoxy]-phenyl}-propionyl-2,3-dihydro-1H-indole-2-carboxylic acid;
(R)-1-(2-{3-[2-(4-Chloro-phenyl)-5-methyl-oxazol-4-ylmethoxy]-phenyl}-2-methyl-propionyl)-2,3-dihydro-1H-indole-2-carboxylic acid; and
(R)-1-(2-{3-[2-(4-Fluoro-phenyl)-5-methyl-oxazol-4-ylmethoxy]-phenyl}-2-methyl-propionyl)-2,3-dihydro-1H-indole-2-carboxylic acid;

or an optical isomer thereof; or a mixture of optical isomers thereof; or a pharmaceutically acceptable salt thereof.

13. A method for the treatment of dyslipidemia, hyperlipidemia, hypercholesteremia, or type-2 diabetes, comprising:
administering to a mammal in need thereof a therapeutically effective amount of a compound of claim 1.

14. A pharmaceutical composition, comprising:
a therapeutically effecflve amount of a compound of claim 1 in combination with one or more pharmaceutically acceptable carriers.

* * * * *

UNITED STATES PATENT AND TRADEMARK OFFICE
CERTIFICATE OF CORRECTION

| | | |
|---|---|---|
| PATENT NO. | : 7,652,061 B2 | Page 1 of 1 |
| APPLICATION NO. | : 10/556988 | |
| DATED | : January 26, 2010 | |
| INVENTOR(S) | : Ksander et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 750 days.

Signed and Sealed this

Ninth Day of November, 2010

David J. Kappos
*Director of the United States Patent and Trademark Office*